(12) United States Patent
Stewart et al.

(10) Patent No.: US 9,743,854 B2
(45) Date of Patent: Aug. 29, 2017

(54) REAL-TIME MORPHOLOGY ANALYSIS FOR LESION ASSESSMENT

(71) Applicant: Boston Scientific Scimed Inc., Maple Grove, MN (US)

(72) Inventors: Brian Stewart, North Reading, MA (US); Adam Magen, Somerville, MA (US); Nathan H. Bennett, Cambridge, MA (US); Michal Weisman, Winchester, MA (US); Paul Hultz, Brookline, NH (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

(21) Appl. No.: 14/975,197

(22) Filed: Dec. 18, 2015

(65) Prior Publication Data

US 2016/0174865 A1    Jun. 23, 2016

Related U.S. Application Data

(60) Provisional application No. 62/093,771, filed on Dec. 18, 2014.

(51) Int. Cl.
| | |
|---|---|
| *A61B 5/042* | (2006.01) |
| *A61B 5/00* | (2006.01) |
| *A61B 5/04* | (2006.01) |
| *A61B 5/044* | (2006.01) |
| *A61B 18/14* | (2006.01) |
| *A61B 18/00* | (2006.01) |

(52) U.S. Cl.
CPC ............ *A61B 5/0422* (2013.01); *A61B 5/044* (2013.01); *A61B 5/04017* (2013.01); *A61B 5/6852* (2013.01); *A61B 18/1492* (2013.01); *A61B 2018/00357* (2013.01); *A61B 2018/00577* (2013.01); *A61B 2018/00779* (2013.01); *A61B 2018/00839* (2013.01)

(58) Field of Classification Search
None
See application file for complete search history.

(56) References Cited

U.S. PATENT DOCUMENTS

| | | | |
|---|---|---|---|
| 3,773,401 | A | 11/1973 | Douklias et al. |
| 4,466,443 | A | 8/1984 | Utsugi |
| 4,602,624 | A | 7/1986 | Naples et al. |

(Continued)

FOREIGN PATENT DOCUMENTS

| | | |
|---|---|---|
| CA | 2682055 A1 | 10/2008 |
| CA | 2847846 A1 | 3/2013 |

(Continued)

OTHER PUBLICATIONS

International Preliminary Report on Patentability issued in PCT/US2015/021300 mailed Sep. 29, 2016, 7 pages.

(Continued)

*Primary Examiner* — Brian T Gedeon
(74) *Attorney, Agent, or Firm* — Faegre Baker Daniels LLP

(57) ABSTRACT

Electrodes are used to measure an electrical signal (e.g., an electrogram). One or more filters are applied to the electrical signal to generate one or more filtered signals. Features of the filtered signals are evaluated to assess a sharpness corresponding to the electrical signal. Based on the sharpness, various characteristics of a morphology of the electrogram may be evaluated over a time period.

20 Claims, 6 Drawing Sheets

(56) References Cited

U.S. PATENT DOCUMENTS

| | | |
|---|---|---|
| 4,633,882 A | 1/1987 | Matsuo et al. |
| 4,732,149 A | 3/1988 | Sutter |
| 4,763,660 A | 8/1988 | Kroll et al. |
| 4,966,145 A | 10/1990 | Kikumoto et al. |
| 5,019,076 A | 5/1991 | Yamanashi et al. |
| 5,029,588 A | 7/1991 | Yock et al. |
| 5,178,150 A | 1/1993 | Silverstein et al. |
| 5,217,460 A | 6/1993 | Knoepfler |
| 5,238,004 A | 8/1993 | Sahatjian et al. |
| 5,240,003 A | 8/1993 | Lancee et al. |
| 5,254,088 A | 10/1993 | Lundquist et al. |
| 5,295,482 A | 3/1994 | Clare et al. |
| 5,318,589 A | 6/1994 | Lichtman |
| 5,324,284 A | 6/1994 | Imran |
| 5,331,966 A | 7/1994 | Bennett et al. |
| 5,334,193 A | 8/1994 | Nardella |
| 5,341,807 A | 8/1994 | Nardella |
| 5,377,685 A | 1/1995 | Kazi et al. |
| 5,383,874 A | 1/1995 | Jackson et al. |
| 5,385,146 A | 1/1995 | Goldreyer |
| 5,385,148 A | 1/1995 | Lesh et al. |
| 5,391,199 A | 2/1995 | Ben-Haim |
| 5,398,683 A | 3/1995 | Edwards et al. |
| 5,423,811 A | 6/1995 | Imran et al. |
| 5,447,529 A | 9/1995 | Marchlinski et al. |
| 5,462,521 A | 10/1995 | Brucker et al. |
| 5,482,054 A | 1/1996 | Slater et al. |
| 5,485,849 A | 1/1996 | Panescu et al. |
| 5,494,042 A | 2/1996 | Panescu et al. |
| 5,500,012 A | 3/1996 | Brucker et al. |
| 5,520,683 A | 5/1996 | Subramaniam et al. |
| 5,571,088 A | 11/1996 | Lennox et al. |
| 5,573,535 A | 11/1996 | Viklund |
| 5,575,772 A | 11/1996 | Lennox |
| 5,579,764 A | 12/1996 | Goldreyer |
| 5,582,609 A | 12/1996 | Swanson et al. |
| 5,647,870 A | 7/1997 | Kordis et al. |
| 5,718,701 A | 2/1998 | Shai et al. |
| 5,722,402 A | 3/1998 | Swanson et al. |
| 5,762,067 A | 6/1998 | Dunham et al. |
| 5,788,636 A | 8/1998 | Curley |
| 5,792,064 A | 8/1998 | Panescu et al. |
| 5,800,482 A | 9/1998 | Pomeranz et al. |
| 5,820,568 A | 10/1998 | Willis |
| 5,830,213 A | 11/1998 | Panescu et al. |
| 5,833,621 A | 11/1998 | Panescu et al. |
| 5,836,990 A | 11/1998 | Li |
| 5,868,735 A | 2/1999 | Lafontaine |
| 5,871,483 A | 2/1999 | Jackson et al. |
| 5,871,526 A | 2/1999 | Gibbs et al. |
| 5,876,336 A | 3/1999 | Swanson et al. |
| 5,885,278 A | 3/1999 | Fleischman |
| 5,913,856 A | 6/1999 | Chia et al. |
| 5,916,213 A | 6/1999 | Haissaguerre et al. |
| 5,957,850 A | 9/1999 | Marian et al. |
| 6,004,269 A | 12/1999 | Crowley et al. |
| 6,027,500 A | 2/2000 | Buckles et al. |
| 6,050,267 A | 4/2000 | Nardella et al. |
| 6,050,994 A | 4/2000 | Sherman |
| 6,059,778 A | 5/2000 | Sherman |
| 6,063,078 A | 5/2000 | Wittkampf |
| 6,064,905 A | 5/2000 | Webster, Jr. et al. |
| 6,068,629 A | 5/2000 | Haissaguerre et al. |
| 6,070,094 A | 5/2000 | Swanson et al. |
| 6,083,170 A | 7/2000 | Ben-Haim |
| 6,083,222 A | 7/2000 | Klein et al. |
| 6,099,524 A | 8/2000 | Lipson et al. |
| 6,101,409 A | 8/2000 | Swanson et al. |
| 6,116,027 A | 9/2000 | Smith et al. |
| 6,120,476 A | 9/2000 | Fung et al. |
| 6,165,123 A | 12/2000 | Thompson |
| 6,171,305 B1 | 1/2001 | Sherman |
| 6,200,314 B1 | 3/2001 | Sherman |
| 6,206,831 B1 | 3/2001 | Suorsa et al. |
| 6,210,337 B1 | 4/2001 | Dunham et al. |
| 6,216,027 B1 | 4/2001 | Willis et al. |
| 6,224,557 B1 | 5/2001 | Ziel et al. |
| 6,233,491 B1 | 5/2001 | Kordis et al. |
| 6,241,754 B1 | 6/2001 | Swanson et al. |
| 6,270,493 B1 | 8/2001 | Lalonde et al. |
| 6,290,697 B1 | 9/2001 | Tu et al. |
| 6,352,534 B1 | 3/2002 | Paddock et al. |
| 6,395,325 B1 | 5/2002 | Hedge et al. |
| 6,400,981 B1 | 6/2002 | Govari |
| 6,423,002 B1 | 7/2002 | Hossack |
| 6,475,213 B1 | 11/2002 | Whayne et al. |
| 6,488,678 B2 | 12/2002 | Sherman |
| 6,491,710 B2 | 12/2002 | Satake |
| 6,508,767 B2 | 1/2003 | Burns et al. |
| 6,508,769 B2 | 1/2003 | Bonnefous |
| 6,508,803 B1 | 1/2003 | Horikawa et al. |
| 6,516,667 B1 | 2/2003 | Broad et al. |
| 6,517,533 B1 | 2/2003 | Swaminathan |
| 6,517,534 B1 | 2/2003 | McGovern et al. |
| 6,537,271 B1 | 3/2003 | Murray et al. |
| 6,544,175 B1 | 4/2003 | Newman |
| 6,546,270 B1 | 4/2003 | Goldin et al. |
| 6,547,788 B1 | 4/2003 | Maguire et al. |
| 6,569,160 B1 | 5/2003 | Goldin et al. |
| 6,572,547 B2 | 6/2003 | Miller et al. |
| 6,575,966 B2 | 6/2003 | Lane et al. |
| 6,575,969 B1 | 6/2003 | Rittman et al. |
| 6,579,278 B1 | 6/2003 | Bencini |
| 6,582,372 B2 | 6/2003 | Poland |
| 6,584,345 B2 | 6/2003 | Govari |
| 6,589,182 B1 | 7/2003 | Loftman et al. |
| 6,592,525 B2 | 7/2003 | Miller et al. |
| 6,602,242 B1 | 8/2003 | Fung et al. |
| 6,620,103 B1 | 9/2003 | Bruce et al. |
| 6,632,179 B2 | 10/2003 | Wilson et al. |
| 6,638,222 B2 | 10/2003 | Chandrasekaran et al. |
| 6,640,120 B1 | 10/2003 | Swanson et al. |
| 6,647,281 B2 | 11/2003 | Morency |
| 6,656,174 B1 | 12/2003 | Hegde et al. |
| 6,658,279 B2 | 12/2003 | Swanson et al. |
| 6,663,573 B2 | 12/2003 | Goldin |
| 6,666,862 B2 | 12/2003 | Jain et al. |
| 6,676,606 B2 | 1/2004 | Simpson et al. |
| 6,692,441 B1 | 2/2004 | Poland et al. |
| 6,705,992 B2 | 3/2004 | Gatzke |
| 6,709,396 B2 | 3/2004 | Flesch et al. |
| 6,711,429 B1 | 3/2004 | Gilboa et al. |
| 6,719,756 B1 | 4/2004 | Muntermann |
| 6,735,465 B2 | 5/2004 | Panescu |
| 6,736,814 B2 | 5/2004 | Manna et al. |
| 6,743,174 B2 | 6/2004 | Ng et al. |
| 6,773,402 B2 | 8/2004 | Govari et al. |
| 6,776,758 B2 | 8/2004 | Peszynski et al. |
| 6,796,979 B2 | 9/2004 | Lentz |
| 6,796,980 B2 | 9/2004 | Hall |
| 6,804,545 B2 | 10/2004 | Fuimaono et al. |
| 6,811,550 B2 | 11/2004 | Holland et al. |
| 6,824,517 B2 | 11/2004 | Salgo et al. |
| 6,837,884 B2 | 1/2005 | Woloszko |
| 6,845,257 B2 | 1/2005 | Fuimaono et al. |
| 6,845,264 B1 | 1/2005 | Skladnev et al. |
| 6,917,834 B2 | 7/2005 | Koblish et al. |
| 6,922,579 B2 | 7/2005 | Taimisto et al. |
| 6,923,808 B2 | 8/2005 | Taimisto |
| 6,932,811 B2 | 8/2005 | Hooven et al. |
| 6,945,938 B2 | 9/2005 | Grunwald |
| 6,950,689 B1 | 9/2005 | Willis et al. |
| 6,952,615 B2 | 10/2005 | Satake |
| 6,958,040 B2 | 10/2005 | Oliver et al. |
| 7,001,383 B2 | 2/2006 | Keidar |
| 7,037,264 B2 | 5/2006 | Poland |
| 7,047,068 B2 | 5/2006 | Haissaguerre |
| 7,097,643 B2 | 8/2006 | Cornelius et al. |
| 7,099,711 B2 | 8/2006 | Fuimaono et al. |
| 7,105,122 B2 | 9/2006 | Karason |
| 7,112,198 B2 | 9/2006 | Satake |
| 7,115,122 B1 | 10/2006 | Swanson et al. |
| 7,123,951 B2 | 10/2006 | Fuimaono et al. |
| 7,131,947 B2 | 11/2006 | Demers |

(56) References Cited

U.S. PATENT DOCUMENTS

| | | |
|---|---|---|
| 7,166,075 B2 | 1/2007 | Varghese et al. |
| 7,181,262 B2 | 2/2007 | Fuimaono et al. |
| 7,220,233 B2 | 5/2007 | Nita et al. |
| 7,232,433 B1 | 6/2007 | Schlesinger et al. |
| 7,247,155 B2 | 7/2007 | Hoey et al. |
| 7,270,634 B2 | 9/2007 | Scampini et al. |
| 7,288,088 B2 | 10/2007 | Swanson |
| 7,291,142 B2 | 11/2007 | Eberl et al. |
| 7,306,561 B2 | 12/2007 | Sathyanarayana |
| 7,335,052 B2 | 2/2008 | D'Sa |
| 7,347,820 B2 | 3/2008 | Bonnefous |
| 7,347,821 B2 | 3/2008 | Dkyba et al. |
| 7,347,857 B2 | 3/2008 | Anderson et al. |
| 7,361,144 B2 | 4/2008 | Levrier et al. |
| 7,422,591 B2 | 9/2008 | Phan |
| 7,438,714 B2 | 10/2008 | Phan |
| 7,455,669 B2 | 11/2008 | Swanson |
| 7,488,289 B2 | 2/2009 | Suorsa et al. |
| 7,507,205 B2 | 3/2009 | Borovsky et al. |
| 7,519,410 B2 | 4/2009 | Taimisto et al. |
| 7,529,393 B2 | 5/2009 | Peszynski et al. |
| 7,534,207 B2 | 5/2009 | Shehada et al. |
| 7,544,164 B2 | 6/2009 | Knowles et al. |
| 7,549,988 B2 | 6/2009 | Eberl et al. |
| 7,569,052 B2 | 8/2009 | Phan et al. |
| 7,578,791 B2 | 8/2009 | Rafter |
| 7,582,083 B2 | 9/2009 | Swanson |
| 7,585,310 B2 | 9/2009 | Phan et al. |
| 7,610,073 B2 | 10/2009 | Fuimaono et al. |
| 7,648,462 B2 | 1/2010 | Jenkins et al. |
| 7,697,972 B2 | 4/2010 | Verard et al. |
| 7,704,208 B2 | 4/2010 | Thiele |
| 7,720,420 B2 | 5/2010 | Kajita |
| 7,727,231 B2 | 6/2010 | Swanson |
| 7,736,362 B2 | 6/2010 | Eberl et al. |
| 7,740,629 B2 | 6/2010 | Anderson et al. |
| 7,758,508 B1 | 7/2010 | Thiele et al. |
| 7,766,833 B2 | 8/2010 | Lee et al. |
| 7,776,033 B2 | 8/2010 | Swanson |
| 7,785,324 B2 | 8/2010 | Eberl |
| 7,794,398 B2 | 9/2010 | Salgo |
| 7,796,789 B2 | 9/2010 | Salgo et al. |
| 7,799,025 B2 | 9/2010 | Wellman |
| 7,815,572 B2 | 10/2010 | Loupas |
| 7,819,863 B2 | 10/2010 | Eggers et al. |
| 7,837,624 B1 | 11/2010 | Hossack et al. |
| 7,859,170 B2 | 12/2010 | Knowles et al. |
| 7,862,561 B2 | 1/2011 | Swanson et al. |
| 7,862,562 B2 | 1/2011 | Eberl |
| 7,879,029 B2 | 2/2011 | Jimenez |
| 7,892,228 B2 | 2/2011 | Landis et al. |
| 7,894,871 B2 | 2/2011 | Wittkampf et al. |
| 7,918,850 B2 | 4/2011 | Govari et al. |
| 7,957,817 B1 | 6/2011 | Gillespie et al. |
| 7,996,085 B2 | 8/2011 | Levin |
| 8,016,822 B2 | 9/2011 | Swanson |
| 8,048,028 B2 | 11/2011 | Horn et al. |
| 8,103,327 B2 | 1/2012 | Harlev et al. |
| 8,128,617 B2 | 3/2012 | Bencini et al. |
| 8,160,690 B2 | 4/2012 | Wilfley et al. |
| 8,162,935 B2 | 4/2012 | Paul et al. |
| 8,265,745 B2 | 9/2012 | Hauck et al. |
| 8,267,926 B2 | 9/2012 | Paul et al. |
| 8,290,578 B2 | 10/2012 | Schneider |
| 8,317,783 B2 | 11/2012 | Cao et al. |
| 8,369,922 B2 | 2/2013 | Paul et al. |
| 8,400,164 B2 | 3/2013 | Osadchy et al. |
| 8,403,925 B2 | 3/2013 | Miller et al. |
| 8,406,866 B2 | 3/2013 | Deno et al. |
| 8,414,579 B2 | 4/2013 | Kim et al. |
| 8,449,535 B2 | 5/2013 | Deno et al. |
| 8,454,538 B2 | 6/2013 | Wittkampf et al. |
| 8,454,589 B2 | 6/2013 | Deno et al. |
| 8,489,184 B2 | 7/2013 | Wilfley et al. |
| 8,579,889 B2 | 11/2013 | Bencini |
| 8,583,215 B2 | 11/2013 | Lichtenstein |
| 8,603,084 B2 | 12/2013 | Fish et al. |
| 8,603,085 B2 | 12/2013 | Jimenez |
| 8,644,950 B2 | 2/2014 | Hauck |
| 8,657,814 B2 | 2/2014 | Werneth et al. |
| 8,672,936 B2 | 3/2014 | Thao et al. |
| 8,679,109 B2 | 3/2014 | Paul et al. |
| 8,728,077 B2 | 5/2014 | Paul et al. |
| 8,740,900 B2 | 6/2014 | Kim et al. |
| 8,755,860 B2 | 6/2014 | Paul et al. |
| 8,771,343 B2 | 7/2014 | Weber et al. |
| 8,876,817 B2 | 11/2014 | Avitall et al. |
| 8,894,643 B2 | 11/2014 | Watson et al. |
| 8,906,011 B2 | 12/2014 | Gelbart et al. |
| 8,945,015 B2 | 2/2015 | Rankin et al. |
| 8,998,890 B2 | 4/2015 | Paul et al. |
| 9,089,340 B2 | 7/2015 | Hastings et al. |
| 9,125,565 B2 | 9/2015 | Hauck |
| 9,125,668 B2 | 9/2015 | Subramaniam et al. |
| 9,168,004 B2 | 10/2015 | Gliner et al. |
| 9,173,586 B2 | 11/2015 | Deno et al. |
| 9,211,156 B2 | 12/2015 | Kim et al. |
| 9,241,687 B2 | 1/2016 | McGee |
| 9,241,761 B2 | 1/2016 | Rankin et al. |
| 9,254,163 B2 | 2/2016 | Paul et al. |
| 9,265,434 B2 | 2/2016 | Merschon et al. |
| 9,271,782 B2 | 3/2016 | Paul et al. |
| 9,283,026 B2 | 3/2016 | Paul et al. |
| 9,370,329 B2 | 6/2016 | Tun et al. |
| 9,393,072 B2 | 7/2016 | Kim et al. |
| 9,463,064 B2 | 10/2016 | Subramaniam et al. |
| 2001/0029371 A1 | 10/2001 | Kordis |
| 2002/0087208 A1 | 7/2002 | Koblish et al. |
| 2002/0165448 A1 | 11/2002 | Ben-Haim et al. |
| 2002/0198521 A1 | 12/2002 | Maguire |
| 2003/0013958 A1 | 1/2003 | Govari et al. |
| 2003/0088240 A1 | 5/2003 | Saadat |
| 2003/0158548 A1 | 8/2003 | Phan et al. |
| 2003/0158549 A1 | 8/2003 | Swanson |
| 2003/0229286 A1 | 12/2003 | Lenker |
| 2004/0006268 A1 | 1/2004 | Gilboa et al. |
| 2004/0082860 A1 | 4/2004 | Haissaguerre |
| 2004/0092806 A1 | 5/2004 | Sagon et al. |
| 2004/0116793 A1 | 6/2004 | Taimisto et al. |
| 2004/0147920 A1 | 7/2004 | Keidar |
| 2004/0162556 A1 | 8/2004 | Swanson |
| 2004/0186467 A1 | 9/2004 | Swanson et al. |
| 2004/0210136 A1 | 10/2004 | Varghese et al. |
| 2004/0215177 A1 | 10/2004 | Swanson |
| 2004/0215186 A1 | 10/2004 | Cornelius et al. |
| 2005/0033331 A1 | 2/2005 | Burnett et al. |
| 2005/0059862 A1 | 3/2005 | Phan |
| 2005/0059962 A1 | 3/2005 | Phan et al. |
| 2005/0059963 A1 | 3/2005 | Phan et al. |
| 2005/0059965 A1 | 3/2005 | Eberl et al. |
| 2005/0065506 A1 | 3/2005 | Phan |
| 2005/0065508 A1 | 3/2005 | Johnson et al. |
| 2005/0070894 A1 | 3/2005 | McClurken |
| 2005/0090817 A1 | 4/2005 | Phan |
| 2005/0119545 A1 | 6/2005 | Swanson |
| 2005/0119648 A1 | 6/2005 | Swanson |
| 2005/0119649 A1 | 6/2005 | Swanson |
| 2005/0119653 A1 | 6/2005 | Swanson |
| 2005/0119654 A1 | 6/2005 | Swanson et al. |
| 2005/0124881 A1 | 6/2005 | Kanai et al. |
| 2005/0187544 A1 | 8/2005 | Swanson et al. |
| 2005/0203597 A1 | 9/2005 | Yamazaki et al. |
| 2005/0228286 A1 | 10/2005 | Messerly et al. |
| 2005/0228504 A1 | 10/2005 | Demarais |
| 2005/0273060 A1 | 12/2005 | Levy et al. |
| 2006/0030919 A1 | 2/2006 | Mrva et al. |
| 2006/0089634 A1 | 4/2006 | Anderson et al. |
| 2006/0100522 A1 | 5/2006 | Yuan et al. |
| 2006/0161146 A1 | 7/2006 | Cornelius et al. |
| 2006/0247607 A1 | 11/2006 | Cornelius et al. |
| 2006/0247683 A1 | 11/2006 | Danek et al. |
| 2006/0253028 A1 | 11/2006 | Lam et al. |
| 2006/0253116 A1 | 11/2006 | Avitall et al. |
| 2007/0003811 A1 | 1/2007 | Zerfass et al. |

(56) References Cited

U.S. PATENT DOCUMENTS

| | | |
|---|---|---|
| 2007/0016054 A1 | 1/2007 | Yuan et al. |
| 2007/0016059 A1 | 1/2007 | Morimoto et al. |
| 2007/0016228 A1 | 1/2007 | Salas |
| 2007/0021744 A1 | 1/2007 | Creighton |
| 2007/0049925 A1 | 3/2007 | Phan et al. |
| 2007/0055225 A1 | 3/2007 | Dodd, III et al. |
| 2007/0073135 A1 | 3/2007 | Lee et al. |
| 2007/0088345 A1 | 4/2007 | Larson et al. |
| 2007/0165916 A1 | 7/2007 | Cloutier et al. |
| 2007/0167813 A1 | 7/2007 | Lee et al. |
| 2007/0181139 A1 | 8/2007 | Hauck |
| 2007/0225610 A1 | 9/2007 | Mickley et al. |
| 2007/0238997 A1 | 10/2007 | Camus |
| 2007/0270794 A1 | 11/2007 | Anderson et al. |
| 2008/0009733 A1 | 1/2008 | Saksena |
| 2008/0015568 A1 | 1/2008 | Paul et al. |
| 2008/0025145 A1 | 1/2008 | Peszynski et al. |
| 2008/0051841 A1 | 2/2008 | Swerdlow et al. |
| 2008/0058836 A1 | 3/2008 | Moll et al. |
| 2008/0086073 A1 | 4/2008 | McDaniel |
| 2008/0091109 A1 | 4/2008 | Abraham |
| 2008/0140065 A1 | 6/2008 | Rioux et al. |
| 2008/0161705 A1 | 7/2008 | Podmore et al. |
| 2008/0161795 A1 | 7/2008 | Wang et al. |
| 2008/0161796 A1 | 7/2008 | Cao et al. |
| 2008/0195089 A1 | 8/2008 | Thiagalingam et al. |
| 2008/0228111 A1 | 9/2008 | Nita |
| 2008/0243214 A1 | 10/2008 | Koblish |
| 2008/0275428 A1 | 11/2008 | Tegg et al. |
| 2008/0281322 A1 | 11/2008 | Sherman et al. |
| 2008/0287803 A1 | 11/2008 | Li et al. |
| 2008/0300454 A1 | 12/2008 | Goto |
| 2008/0312521 A1 | 12/2008 | Solomon |
| 2008/0312713 A1 | 12/2008 | Wilfley et al. |
| 2009/0005771 A1 | 1/2009 | Lieber et al. |
| 2009/0030312 A1 | 1/2009 | Hadjicostis |
| 2009/0048591 A1 | 2/2009 | Ibrahim et al. |
| 2009/0056344 A1 | 3/2009 | Poch |
| 2009/0062790 A1 | 3/2009 | Malchano et al. |
| 2009/0062795 A1 | 3/2009 | Vakharia et al. |
| 2009/0076390 A1 | 3/2009 | Lee et al. |
| 2009/0093810 A1 | 4/2009 | Subramaniam et al. |
| 2009/0093811 A1 | 4/2009 | Koblish et al. |
| 2009/0099472 A1 | 4/2009 | Remmert et al. |
| 2009/0131932 A1 | 5/2009 | Vakharia et al. |
| 2009/0163904 A1 | 6/2009 | Miller et al. |
| 2009/0171341 A1 | 7/2009 | Pope et al. |
| 2009/0171345 A1 | 7/2009 | Miller et al. |
| 2009/0177069 A1 | 7/2009 | Razavi |
| 2009/0177111 A1 | 7/2009 | Miller et al. |
| 2009/0182316 A1 | 7/2009 | Bencini |
| 2009/0209950 A1 | 8/2009 | Starksen |
| 2009/0216125 A1 | 8/2009 | Lenker |
| 2009/0240247 A1 | 9/2009 | Rioux et al. |
| 2009/0259274 A1 | 10/2009 | Simon et al. |
| 2009/0275827 A1 | 11/2009 | Aiken et al. |
| 2009/0281541 A1 | 11/2009 | Ibrahim et al. |
| 2009/0287202 A1 | 11/2009 | Ingle et al. |
| 2009/0292209 A1 | 11/2009 | Hadjicostis |
| 2009/0299355 A1 | 12/2009 | Bencini et al. |
| 2009/0299360 A1 | 12/2009 | Ormsby |
| 2009/0306643 A1 | 12/2009 | Pappone et al. |
| 2010/0010487 A1 | 1/2010 | Phan et al. |
| 2010/0057072 A1 | 3/2010 | Roman et al. |
| 2010/0076402 A1 | 3/2010 | Mazzone et al. |
| 2010/0094274 A1 | 4/2010 | Narayan et al. |
| 2010/0106155 A1 | 4/2010 | Anderson et al. |
| 2010/0113938 A1 | 5/2010 | Park et al. |
| 2010/0145221 A1 | 6/2010 | Brunnett et al. |
| 2010/0152728 A1 | 6/2010 | Park et al. |
| 2010/0168557 A1 | 7/2010 | Deno et al. |
| 2010/0168568 A1 | 7/2010 | Sliwa |
| 2010/0168570 A1 | 7/2010 | Sliwa et al. |
| 2010/0168831 A1 | 7/2010 | Korivi et al. |
| 2010/0241117 A1 | 9/2010 | Paul et al. |
| 2010/0249599 A1 | 9/2010 | Hastings et al. |
| 2010/0249603 A1 | 9/2010 | Hastings et al. |
| 2010/0249604 A1 | 9/2010 | Hastings et al. |
| 2010/0298826 A1 | 11/2010 | Leo et al. |
| 2010/0331658 A1 | 12/2010 | Kim et al. |
| 2011/0028820 A1 | 2/2011 | Lau et al. |
| 2011/0034915 A1 | 2/2011 | Ibrahim et al. |
| 2011/0071400 A1 | 3/2011 | Hastings et al. |
| 2011/0071401 A1 | 3/2011 | Hastings et al. |
| 2011/0112569 A1 | 5/2011 | Friedman et al. |
| 2011/0125143 A1 | 5/2011 | Gross et al. |
| 2011/0130648 A1 | 6/2011 | Beeckler et al. |
| 2011/0137153 A1 | 6/2011 | Govari et al. |
| 2011/0144491 A1 | 6/2011 | Sliwa et al. |
| 2011/0144524 A1 | 6/2011 | Fish et al. |
| 2011/0160584 A1 | 6/2011 | Paul et al. |
| 2011/0237933 A1 | 9/2011 | Cohen |
| 2011/0282249 A1 | 11/2011 | Tsoref et al. |
| 2011/0319782 A1 | 12/2011 | Sweeney et al. |
| 2012/0004547 A1 | 1/2012 | Harks et al. |
| 2012/0095347 A1 | 4/2012 | Adam et al. |
| 2012/0101398 A1 | 4/2012 | Ramanathan et al. |
| 2012/0116537 A1 | 5/2012 | Liebetanz |
| 2012/0136346 A1 | 5/2012 | Condie et al. |
| 2012/0136348 A1 | 5/2012 | Condie et al. |
| 2012/0136351 A1 | 5/2012 | Weekamp et al. |
| 2012/0172698 A1 | 7/2012 | Hastings et al. |
| 2012/0172727 A1 | 7/2012 | Hastings et al. |
| 2012/0172871 A1 | 7/2012 | Hastings et al. |
| 2012/0238897 A1 | 9/2012 | Wilfley et al. |
| 2012/0310064 A1 | 12/2012 | McGee |
| 2012/0330304 A1 | 12/2012 | Vegesna et al. |
| 2013/0023784 A1 | 1/2013 | Schneider et al. |
| 2013/0023897 A1 | 1/2013 | Wallace |
| 2013/0060245 A1 | 3/2013 | Grunewald et al. |
| 2013/0066312 A1 | 3/2013 | Subramaniam et al. |
| 2013/0066315 A1 | 3/2013 | Subramaniam et al. |
| 2013/0079763 A1 | 3/2013 | Heckel et al. |
| 2013/0165926 A1 | 6/2013 | Mathur et al. |
| 2013/0172715 A1 | 7/2013 | Just et al. |
| 2013/0172742 A1 | 7/2013 | Rankin et al. |
| 2013/0172875 A1 | 7/2013 | Govari et al. |
| 2013/0184706 A1 | 7/2013 | Gelbart et al. |
| 2013/0190747 A1 | 7/2013 | Koblish et al. |
| 2013/0197363 A1 | 8/2013 | Rankin et al. |
| 2013/0226169 A1 | 8/2013 | Miller et al. |
| 2013/0274582 A1 | 10/2013 | Afonso et al. |
| 2013/0331739 A1 | 12/2013 | Gertner |
| 2013/0345537 A1 | 12/2013 | Thakur et al. |
| 2014/0012251 A1 | 1/2014 | Himmelstein et al. |
| 2014/0058375 A1 | 2/2014 | Koblish |
| 2014/0066764 A1 | 3/2014 | Subramaniam et al. |
| 2014/0073893 A1 | 3/2014 | Bencini |
| 2014/0075753 A1 | 3/2014 | Haarer et al. |
| 2014/0081111 A1 | 3/2014 | Tun et al. |
| 2014/0081112 A1 | 3/2014 | Kim et al. |
| 2014/0081113 A1 | 3/2014 | Cohen et al. |
| 2014/0081262 A1 | 3/2014 | Koblish et al. |
| 2014/0100563 A1 | 4/2014 | Govari et al. |
| 2014/0107453 A1 | 4/2014 | Maskara et al. |
| 2014/0107636 A1 | 4/2014 | Bencini |
| 2014/0128757 A1 | 5/2014 | Banet et al. |
| 2014/0194867 A1 | 7/2014 | Fish et al. |
| 2014/0200429 A1 | 7/2014 | Spector et al. |
| 2014/0200430 A1 | 7/2014 | Spector |
| 2014/0214028 A1 | 7/2014 | Gelbart et al. |
| 2014/0228713 A1 | 8/2014 | Thao et al. |
| 2014/0243917 A1 | 8/2014 | Morley et al. |
| 2014/0261985 A1 | 9/2014 | Selkee |
| 2014/0276052 A1 | 9/2014 | Rankin et al. |
| 2014/0276811 A1 | 9/2014 | Koblish et al. |
| 2014/0330150 A1 | 11/2014 | Thakur et al. |
| 2014/0336518 A1 | 11/2014 | Shuros et al. |
| 2014/0364715 A1 | 12/2014 | Hauck |
| 2014/0364843 A1 | 12/2014 | Paul et al. |
| 2014/0364848 A1 | 12/2014 | Heimbecher et al. |
| 2015/0005624 A1 | 1/2015 | Hauck et al. |
| 2015/0011995 A1 | 1/2015 | Avitall et al. |
| 2015/0018813 A1 | 1/2015 | Gliner |

(56) References Cited

U.S. PATENT DOCUMENTS

| | | |
|---|---|---|
| 2015/0133914 A1 | 5/2015 | Koblish |
| 2015/0133920 A1 | 5/2015 | Rankin et al. |
| 2015/0265341 A1 | 9/2015 | Koblish |
| 2015/0265348 A1 | 9/2015 | Avitall et al. |
| 2015/0342672 A1 | 12/2015 | Bencini et al. |
| 2015/0374436 A1 | 12/2015 | Subramaniam et al. |
| 2016/0008065 A1 | 1/2016 | Gliner et al. |
| 2016/0100884 A1 | 4/2016 | Fay et al. |
| 2016/0113712 A1 | 4/2016 | Cheung et al. |

FOREIGN PATENT DOCUMENTS

| | | |
|---|---|---|
| CA | 2848053 A1 | 3/2013 |
| CN | 1269708 A | 10/2000 |
| CN | 1455655 A | 11/2003 |
| CN | 1942145 A | 4/2007 |
| CN | 102271607 A | 12/2011 |
| CN | 102573986 A | 7/2012 |
| CN | 103917185 A | 7/2014 |
| CN | 103987336 A | 8/2014 |
| CN | 104619259 A | 5/2015 |
| CN | 104640513 A | 5/2015 |
| CN | 104661609 A | 5/2015 |
| EP | 1343426 B1 | 9/2003 |
| EP | 1343427 E1 | 9/2003 |
| EP | 1502542 A1 | 2/2005 |
| EP | 1547537 A1 | 6/2005 |
| EP | 0985423 B1 | 4/2006 |
| EP | 1717601 A2 | 11/2006 |
| EP | 1935332 A2 | 6/2008 |
| EP | 2755587 A | 7/2014 |
| EP | 2755588 A | 7/2014 |
| EP | 2136702 B1 | 7/2015 |
| EP | 2897545 A1 | 7/2015 |
| JP | 2000000242 A | 1/2000 |
| JP | 200083918 A | 3/2000 |
| JP | 2000504242 A | 4/2000 |
| JP | 2002528039 A | 8/2002 |
| JP | 2003504090 A | 2/2003 |
| JP | 2004503335 A | 2/2004 |
| JP | 2006239414 A | 9/2006 |
| JP | 2007163559 A | 6/2007 |
| JP | 2007244857 A | 9/2007 |
| JP | 2009142653 A | 12/2008 |
| JP | 2009518150 A | 5/2009 |
| JP | 2010522623 A | 7/2010 |
| JP | 2011142995 A | 7/2011 |
| JP | 2011525842 A | 9/2011 |
| JP | 2012531967 A | 12/2012 |
| JP | 5336465 B2 | 11/2013 |
| JP | 2014012174 A | 1/2014 |
| JP | 2014531244 A | 11/2014 |
| JP | 2015501162 A | 1/2015 |
| JP | 2015509027 A | 3/2015 |
| KR | 20100021401 A | 2/2010 |
| KR | 101490374 B1 | 2/2015 |
| WO | WO9221278 A1 | 12/1992 |
| WO | WO9413358 A1 | 6/1994 |
| WO | WO9725916 A1 | 7/1997 |
| WO | WO9725917 A1 | 7/1997 |
| WO | WO9736541 A1 | 10/1997 |
| WO | 9745156 A2 | 12/1997 |
| WO | WO9858681 A2 | 12/1998 |
| WO | 9909879 A1 | 3/1999 |
| WO | WO9927862 A1 | 6/1999 |
| WO | WO0029062 A2 | 5/2000 |
| WO | WO0158372 A1 | 8/2001 |
| WO | WO0164145 A1 | 9/2001 |
| WO | WO0168173 A2 | 9/2001 |
| WO | WO0205868 A2 | 1/2002 |
| WO | WO0209599 A2 | 2/2002 |
| WO | WO0219934 A1 | 3/2002 |
| WO | WO0247569 A1 | 6/2002 |
| WO | WO02102234 A2 | 12/2002 |
| WO | WO03039338 A2 | 5/2003 |
| WO | WO2007079278 A1 | 7/2007 |
| WO | WO2008046031 A2 | 4/2008 |
| WO | WO2008118992 A1 | 10/2008 |
| WO | WO2009032421 A2 | 3/2009 |
| WO | 2009043824 A1 | 4/2009 |
| WO | 2009048943 A1 | 4/2009 |
| WO | 2010054409 A1 | 5/2010 |
| WO | WO2010056771 A1 | 5/2010 |
| WO | 2010082146 A1 | 7/2010 |
| WO | 2011008444 A1 | 1/2011 |
| WO | 2011033421 A1 | 3/2011 |
| WO | WO2011024133 A1 | 3/2011 |
| WO | WO2011089537 A1 | 7/2011 |
| WO | 2011101778 A1 | 8/2011 |
| WO | WO2011095937 A1 | 8/2011 |
| WO | 2012001595 A1 | 1/2012 |
| WO | WO2012001595 A1 | 1/2012 |
| WO | WO2012049621 A1 | 4/2012 |
| WO | WO2012066430 A1 | 5/2012 |
| WO | 2012161880 A1 | 11/2012 |
| WO | WO2012151301 A1 | 11/2012 |
| WO | 2012166239 A1 | 12/2012 |
| WO | 2013040201 A2 | 3/2013 |
| WO | 2013040297 A1 | 3/2013 |
| WO | 2014036439 A2 | 3/2014 |
| WO | 2014058375 A2 | 4/2014 |
| WO | 2014072879 A2 | 5/2014 |
| WO | 2014152575 A2 | 9/2014 |
| WO | 2015143061 A1 | 9/2015 |
| WO | 2015183635 A1 | 12/2015 |

OTHER PUBLICATIONS

International Search Report and Written Opinion issued in PCT/US2015/066874, mailed Apr. 1, 2016, 11 pages.
Extended European Search Report issued in EP Application No. 15174537.9, issued Mar. 2, 2016, 7 pages.
Goldberg, S. Nahum et al., "Variables Affecting Proper System Grounding for Radiofrequency Ablation in an Animal Model", JVIR, vol. 11, No. 8, Sep. 2000, pp. 1069-1075.
Haverkamp, W., et. al. Coagulation of Ventricular Myocardium Using Radiofrequency Alternating Current: Bio-Physical Aspects and Experimental Findings, PACE, 12:187-195, Jan. 1989, Part II.
International Preliminary Examination Report issued in PCT/US2013/060612, completed Mar. 24, 2015, 10 pages.
International Preliminary Report on Patentability issued in PCT/US2008/058324, mailed Sep. 29, 2009, 9 pages.
International Preliminary Report on Patentability issued in PCT/US2012/055155, issued Mar. 18, 2014, 11 pages.
International Preliminary Report on Patentability issued in PCT/US2012/055309, issued on Mar. 18, 2014, 8 pages.
International Preliminary Report on Patentability issued in PCT/US2013/056211, completed Feb. 24, 2015, 5 pages.
International Preliminary Report on Patentability issued in PCT/US2013/058105, completed Mar. 10, 2015.
International Preliminary Report on Patentability issued in PCT/US2013/060194, mailed Mar. 24, 2015, 6 pages.
International Preliminary Report on Patentability issued in PCT/US2014/027491, mailed Sep. 24, 2015, 12 pages.
International Preliminary Report on Patentablity issued in PCT/US2013/060183, mailed Mar. 24, 2015, 6 pages.
International Search Report and Written Opinion issued in PCT/US2008/058324, dated Aug. 18, 2008, 11 pages.
International Search Report and Written Opinion issued in PCT/US2012/031819, mailed Sep. 27, 2012, 16 pages.
International Search Report and Written Opinion issued in PCT/US2012/055155, mailed Mar. 11, 2013, 19 pages.
International Search Report and Written Opinion issued in PCT/US2012/055309, mailed Nov. 19, 2012, 13 pages.
International Search Report and Written Opinion issued in PCT/US2012/072061, mailed Mar. 21, 2013, 9 pages.
International Search Report and Written Opinion issued in PCT/US2013/020503, mailed Mar. 20, 2013, 10 pages.
International Search Report and Written Opinion issued in PCT/US2013/021013, mailed Apr. 5, 2013, 14 pages.

(56) References Cited

OTHER PUBLICATIONS

International Search Report and Written Opinion issued in PCT/US2013/056211, mailed Jan. 20, 2014.
International Search Report and Written Opinion issued in PCT/US2013/058105, mailed Nov. 22, 2013, 16 pages.
International Search Report and Written Opinion issued in PCT/US2013/060183, mailed Jan. 27, 2014, 10 pages.
International Search Report and Written Opinion issued in PCT/US2013/060194, mailed Jan. 29, 2014.
International Search Report and Written Opinion issued in PCT/US2013/060194, mailed Jan. 29, 2014, 10 pages.
International Search Report and Written Opinion issued in PCT/US2013/060612, mailed Feb. 28, 2014, 16 pages.
International Search Report and Written Opinion issued in PCT/US2014/027491, mailed Sep. 23, 2014, 17 pages.
International Search Report and Written Opinion issued in PCT/US2015/021300, mailed Jun. 9, 2015, 11 pages.
International Search Report and Written Opinion issued in PCT/US2015/055173, mailed Jan. 18, 2016, 11 pages.
International Search Report and Written Opinion issued in PCT/US2015/057242, mailed Jan. 15, 2016, 11 pages.
International Search Report and Written Opinion issued in PCT/US2016/028006 mailed Jul. 12, 2016, 12 pages.
International Search Report and Written Opinion issued in PCTUS2015/031591, mailed Aug. 17, 2015, 11 pages.
Invitation to Pay Additional Fees and Partial International Search Report issued in PCT/US2014/027491, mailed Jul. 28, 2014, 5 pages.
Machi MD, Junji, "Prevention of Dispersive Pad Skin Burns During RFA by a Simple Method", Editorial Comment, Surg Laparosc Endosc Percutan Tech, vol. 13, No. 6, Dec. 2003, pp. 372-373.
Neufeld, Gordon R. et al., "Electrical Impedance Properties of the Body and the Problem of Alternate-site Burns During Electrosurgery", Medical Instrumentation, vol. 19, No. 2, Mar.-Apr. 1985, pp. 83-87.
Partial International Search Report issued in PCT/US2012/055155, mailed Dec. 20, 2012, 7 pages.
Patriciu, A. et al., "Detecting Skin Burns induced by Surface Electrodes", published in Engineering in Medicine and Biology Society, 2001. Proceedings of the 23rd Annual International Conference of the IEEE, vol. 3, pp. 3129-3131.
Piorkolwski, Christopher et al., "First in Human Validation of Impedance-Based Catheter Tip-to-Tissue Contact Assessment in the Left Atrium", Journal of Cardiovascular Electrophysiology, vol. 20, No. 12, Dec. 1, 2009, pp. 1366-1373.
Pires, L. A., et. al. Temperature-guided Radiofrequency Catheter Ablation of Closed-Chest Ventricular Myocardium with a Novel Thermistor-Tipped Catheter. American Heart Journal, 127(6):1614-1618, Jun. 1994.
Price, Adam et al., "Novel Ablation Catheter Technology that Improves Mapping Resolution and Monitoring of Lesion Maturation", The Journal of Innovations in Cardiac Rhythm Management, vol. 3, 2002, pp. 599-609.
Price, Adam et al., "PO3-39 Pin Electrodes Improve Resolution: Enhanced Monitoring of Radiofrequency Lesions in the Voltage and Frequency Domains", Heart Rhythm 2010, 31st Annual Scientific Sessions, May 12-15 in Denver Colorado.
Ring, E. R., et. al. Catheter Ablation of the Ventricular Septum with Radiofrequency Energy. American Heart Journal, 117(6)1233-1240, Jun. 1989.
Steinke, Karin et al., "Dispersive Pad Site burns Wth Modern Radiofrequency Ablation Equipment", Surg Laparosc Endosc Percutan Tech, vol. 13, No. 6, Dec. 2003, pp. 366-371.
Zachary, J.M. et al., "PO4-86 Pin Electrodes Provide Enhanced Resolution Enabling Titration of Radiofrequency Duration to Lesion Maturation", Heart Rhythm 2011, 32 Annual Scientific Sessions, May 4-7, San Francisco, CA.
Extended European Search Report issued in EP Application 16182627.6, mailed Nov. 8, 2016, 5 pages.
International Preliminary Report on Patentability issued in PCT/US2015/031591, mailed Dec. 6, 2016, 7 pages.

REAL-TIME MORPHOLOGY ANALYSIS FOR LESION ASSESSMENT

CROSS-REFERENCE TO RELATED APPLICATION

This application claims priority to Provisional Application No. 62/093,771, filed Dec. 18, 2014, which is herein incorporated by reference in its entirety.

TECHNICAL FIELD

The present disclosure relates to therapies for cardiac conditions. More particularly, the present disclosure relates to methods and systems for ablation of cardiac tissue for treating cardiac arrhythmias.

BACKGROUND

Aberrant conductive pathways disrupt the normal path of the heart's electrical impulses. The aberrant conductive pathways can create abnormal, irregular, and sometimes life-threatening heart rhythms called arrhythmias. Ablation is one way of treating arrhythmias and restoring normal conduction. The aberrant pathways, and/or their sources, may be located or mapped using mapping electrodes situated in a desired location. After mapping, the physician may ablate the aberrant tissue. In radio frequency (RF) ablation, RF energy may be directed from the ablation electrode through tissue to another electrode to ablate the tissue and form a lesion.

SUMMARY

Embodiments of the present invention facilitate real-time electrogram morphology analysis. Electrodes are used to measure an electrical signal (e.g., an electrogram), which may be, for example, a unipolar signal, a bipolar signal, and/or the like. In embodiments, an "electrical signal" may be, refer to, and/or include a signal detected by a single electrode (e.g., a unipolar signal), a signal detected by two or more electrodes (e.g., a bipolar signal), a plurality of signals detected by one or more electrodes, and/or the like. One or more filters are applied to the electrical signal to generate one or more filtered signals. Features of the filtered signals are evaluated to assess a sharpness corresponding to the electrical signal. Based on the sharpness, various characteristics of a morphology of the electrogram may be evaluated over a time period.

In Example 1, a system comprises a catheter that includes a flexible catheter body having a distal portion and at least one electrode disposed on the distal portion, the at least one electrode configured to measure an electrical signal based on a cardiac activation signal. The system also includes a mapping processor configured to acquire the electrical signal from the at least one electrode, generate an electrogram based on the electrical signal, determine a sharpness associated with the electrogram, and/or determine, based on the sharpness, a characteristic of a morphology of the electrogram.

In Example 2, the system of Example 1, further comprising a display device configured to display an indication associated with at least one of the sharpness and the characteristic of the morphology of the electrogram, wherein the characteristic of the morphology of the electrogram comprises a feature related to the sharpness; and an output component configured to provide an output to the display device, wherein the output comprises the sharpness and/or the determined feature.

In Example 3, the system of any of Examples 1 and 2, wherein the catheter comprises an ablation catheter including a tissue ablation electrode configured to apply ablation energy to tissue, the system further comprising a radiofrequency (RF) generator operatively coupled to the tissue ablation electrode, wherein the RF generator is configured to generate the ablation energy and convey the generated ablation energy to the tissue ablation electrode.

In Example 4, the system of Example 3, wherein the mapping processor is configured to determine the sharpness before an ablation, during an ablation, and/or after an ablation.

In Example 5, the system of any of Examples 2-4, wherein the mapping processor comprises: a filter configured to filter the electrical signal to generate a filtered signal; and a feature detector configured to determine an amplitude of the filtered signal, wherein the determined feature comprises the determined amplitude of the filtered signal, wherein the display device is configured to indicate a relative change in the amplitude of the filtered signal during a period of time.

In Example 6, the system of Example 5, wherein the amplitude comprises at least one of an absolute amplitude, a root-mean-squared (RMS) measurement, a peak-to-peak measurement, a maximum of a peak-to-peak measurement over a window, a percentile range measurement, a beat-gated measurement, and a free-running measurement.

In Example 7, the system of any of Examples 5 and 6, wherein the filter is more responsive to high-frequency and/or quickly-varying components of the electrical signal than to low-frequency and/or slowly-varying components of the electrical signal.

In Example 8, the system of any of Examples 5-7, wherein the filtered signal comprises an approximate derivative of the electrical signal.

In Example 9, the system of any of Examples 5-8, wherein the filter includes a nonlinear processing element configured to attenuate one or more components of the electrical signal based on a polarity of a deflection of the electrical signal.

In Example 10, the system of Example 9, wherein the filter comprises a half-wave rectifier.

In Example 11, the system of any of Examples 2-10, the mapping processor comprising: a first filter configured to filter the electrical signal across a first time scale to generate a first filtered signal, wherein the first filter comprises a first frequency response; a second filter configured to filter the electrical signal across a second time scale to generate a second filtered signal, wherein the second filter comprises a second frequency response, wherein at least a portion of the frequency response of the second filter is lower than a corresponding portion of the frequency response of the first filter; and a feature detector configured to determine a feature corresponding to sharpness by analyzing the first and second filtered signals, wherein the display device is configured to depict a change in the determined feature over time.

In Example 12, the system of Example 11, wherein at least one of the first and second filters is configured to determine at least one of a time difference of the electrical signal, an approximate derivative of the electrical signal, a slope estimate across a time window, and a wavelet decomposition of the electrical signal.

In Example 13, the system of any of Examples 11 and 12, wherein at least one of the first and second filters is more responsive to high-frequency and/or quickly-varying components of the electrical signal than to low-frequency and/or slowly-varying components of the electrical signal.

In Example 14, the system of any of Examples 1-13, wherein the mapping processor is further configured to determine an overall morphology change of the electrogram based on a pre-ablation deflection template.

In Example 15, the system of Example 14, wherein the change in morphology is determined using at least one of a matched filter, a correlation, and a convolution with the pre-ablation deflection template or a signal derived therefrom.

In Example 16, the system of any of Examples 2-15, wherein the display device is configured to display a waveform.

In Example 17, the system of Example 16, the waveform representing at least one of the filtered signal, an envelope of the filtered signal, an amplitude of the filtered signal, and a power of the filtered signal.

In Example 18, the system of any of Examples 16 and 17, wherein the output component is configured to determine a combined signal comprising a combination of the filtered signal with an additional filtered signal, the waveform representing at least one of the combined signal, an envelope of the combined signal, an amplitude of the combined signal, and a power of the combined signal.

In Example 19, a method for evaluating a condition of myocardial tissue, the method comprising: positioning a catheter adjacent to myocardial tissue within a patient's body, the catheter comprising: a flexible catheter body having a distal portion; and at least one electrode disposed on the distal portion, the at least one electrode configured to measure an electrical signal based on a cardiac activation signal; receiving the electrical signal; providing an electrogram based on the electrical signal; determining at least one of a sharpness of the electrogram and a characteristic of a morphology of the electrogram, the characteristic of the morphology of the electrogram relating to the sharpness; and displaying at least one of an indication of the sharpness and an indication of the characteristic of the morphology, wherein the indication comprises at least one of a map, a light indicator, and a waveform.

In Example 20, the method of Example 19, wherein the catheter comprises an ablation catheter including a tissue ablation electrode configured to apply ablation energy to tissue, the method further comprising performing an ablation of a portion of the tissue.

In Example 21, method of Example 20, further comprising determining the characteristic of the morphology of the electrogram before an ablation, during an ablation, and/or after an ablation.

In Example 22, the method of any of Examples 19-21, further comprising filtering, using a filter, the electrical signal to generate a filtered signal.

In Example 23, the method of Example 22, wherein the electrical signal is unipolar, and wherein filtering the electrical signal comprises applying a nonlinear processing technique to the electrogram to retain only negative deflections.

In Example 24, the method of any of Examples 22 and 23, wherein filtering the electrical signal comprises approximating a derivative of the electrical signal, the method further comprising determining a relative change in an amplitude of the filtered signal during a period of time, wherein the indication of the characteristic of the morphology indicates the relative change in the amplitude of the filtered signal during the period of time.

In Example 25, the method of Example 24, wherein the amplitude comprises at least one of an absolute amplitude, a root-mean-squared (RMS) measurement, a peak-to-peak measurement, a maximum of a peak-to-peak measurement over a window, a percentile range measurement, a beat-gated measurement, and a free-running measurement.

In Example 26, the method of any of Examples 22-25, wherein the filter is more responsive to high-frequency and/or quickly-varying components of the electrical signal than to low-frequency and/or slowly-varying components of the electrical signal.

In Example 27, the method of any of Examples 22-26, wherein the filter includes a nonlinear processing element configured to attenuate one or more components of the electrical signal based on a polarity of a deflection of the electrical signal.

In Example 28, the method of any of Examples 22-27, wherein the filter comprises a half-wave rectifier.

In Example 29, the method of any of Examples 19-28, further comprising: filtering the electrical signal across a first time scale to generate a first filtered signal, wherein the first filter comprises a first frequency response; filtering the electrical signal across a second time scale to generate a second filtered signal, wherein the second filter comprises a second frequency response, wherein at least a portion of the frequency response of the second filter is lower than a corresponding portion of the frequency response of the first filter; determining a feature corresponding to sharpness by analyzing the first and second filtered signals; and providing an output to a display device, wherein the output comprises the determined feature, wherein the display device is configured to depict a change in the determined feature over time.

In Example 30, the method of Example 29, wherein at least one of the first and second filters is configured to determine at least one of a time difference of the electrical signal, a derivative of the electrical signal, a slope estimate across a time window, and a wavelet decomposition of the electrical signal.

In Example 31, the method of any of Examples 29 and 30, wherein at least one of the first and second filters is more responsive to high-frequency and/or quickly-varying components of the electrical signal than to low-frequency and/or slowly-varying components of the electrical signal.

In Example 32, the method of any of Examples 19-31, further comprising determining an overall morphology change of the electrogram based on a pre-ablation deflection template.

In Example 33, the method of Example 32, wherein the change in morphology is determined using at least one of a matched filter, a correlation, and a convolution with the pre-ablation deflection template or a signal derived therefrom.

In Example 34, the method of any of Examples 19-33, the waveform representing at least one of the filtered signal, an envelope of the filtered signal, an amplitude of the filtered signal, and a power of the filtered signal.

In Example 35, the method of any of Examples 19-34, further comprising determining a combined signal comprising a combination of the filtered signal with an additional filtered signal, the waveform representing at least one of the combined signal, an envelope of the combined signal, an amplitude of the combined signal, and a power of the combined signal.

In Example 36, a system includes a catheter including a flexible catheter body having a distal portion; and at least one electrode disposed on the distal portion, the at least one electrode configured to measure an electrical signal based on a cardiac activation signal. The system also includes a mapping processor configured to acquire the electrical signal from the at least one electrode, provide an electrogram based on the electrical signal, determine at least one of a sharpness associated with the electrogram and a characteristic of a morphology of the electrogram, wherein the characteristic of the morphology of the electrogram is related to the sharpness.

In Example 37, the system of Example 36, wherein the catheter comprises an ablation catheter including a tissue ablation electrode configured to apply ablation energy to tissue, the system further comprising a radiofrequency (RF) generator operatively coupled to the tissue ablation electrode, wherein the RF generator is configured to generate the ablation energy and convey the generated ablation energy to the tissue ablation electrode.

In Example 38, the system of Example 37, wherein the mapping processor is configured to determine the sharpness before an ablation, during an ablation, and/or after an ablation.

In Example 39, the system of Example 36, further comprising a display device, wherein the mapping processor comprises: a filter configured to filter the electrical signal to generate a filtered signal; a feature detector configured to determine an amplitude of the filtered signal; and an output component configured to provide an output to the display device, wherein the output comprises the determined amplitude of the filtered signal.

In Example 40, the system of Example 39, wherein the amplitude comprises at least one of an absolute amplitude, a root-mean-squared (RMS) measurement, a peak-to-peak measurement, a maximum of a peak-to-peak measurement over a window, a percentile range measurement, a beat-gated measurement, and a free-running measurement.

In Example 41, the system of Example 39, wherein the filter is more responsive to high-frequency and/or quickly-varying components of the electrical signal than to low-frequency and/or slowly-varying components of the electrical signal.

In Example 42, the system of Example 39, wherein the filtered signal comprises an approximate derivative of the electrical signal.

In Example 43, the system of Example 39, wherein the filter includes a nonlinear processing element configured to attenuate one or more components of the electrical signal based on a polarity of a deflection of the electrical signal.

In Example 44, the system of Example 43, wherein the filter comprises a half-wave rectifier.

In Example 45, the system of Example 39, wherein the display device is configured to indicate a relative change in the amplitude of the filtered signal during a period of time.

In Example 46, the system of Example 39, wherein the display device is configured to display a waveform.

In Example 47, the system of Example 46, the waveform representing at least one of the filtered signal, an envelope of the filtered signal, an amplitude of the filtered signal, and a power of the filtered signal.

In Example 48, the system of Example 46, wherein the output component is configured to determine a combined signal comprising a combination of the filtered signal with an additional filtered signal, the waveform representing at least one of the combined signal, an envelope of the combined signal, an amplitude of the combined signal, and a power of the combined signal.

In Example 49, the system of Example 36, further comprising a display device, the mapping processor comprising: a first filter configured to filter the electrical signal across a first time scale to generate a first filtered signal, wherein the first filter comprises a first frequency response; a second filter configured to filter the electrical signal across a second time scale to generate a second filtered signal, wherein the second filter comprises a second frequency response, wherein at least a portion of the frequency response of the second filter is lower than a corresponding portion of the frequency response of the first filter; a feature detector configured to determine a feature corresponding to sharpness by analyzing the first and second filtered signals; and an output component configured to provide an output to the display device, wherein the output comprises the determined feature, wherein the display device is configured to depict a change in the determined feature over time.

In Example 50, the system of Example 49, wherein at least one of the first and second filters is configured to determine at least one of a time difference of the electrical signal, an approximate derivative of the electrical signal, a slope estimate across a time window, and a wavelet decomposition of the electrical signal.

In Example 51, the system of Example 49, wherein at least one of the first and second filters is more responsive to high-frequency and/or quickly-varying components of the electrical signal than to low-frequency and/or slowly-varying components of the electrical signal.

In Example 52, the system of Example 49, wherein the feature detector is configured to assess the sharpness of the electrical signal by comparing one or more levels of the first filtered signal with one or more levels of the second filtered signal to determine an amplitude-invariant measure of sharpness.

In Example 53, the system of Example 36, wherein the mapping processor is further configured to determine an overall morphology change of the electrogram based on a pre-ablation deflection template.

In Example 54, the system of Example 53, wherein the change in morphology is determined using at least one of a matched filter, a correlation, and a convolution with the pre-ablation deflection template or a signal derived therefrom.

In Example 55, a method for evaluating a condition of myocardial tissue includes positioning a catheter adjacent to myocardial tissue within a patient's body, the catheter including a flexible catheter body having a distal portion, at least one electrode disposed on the distal portion, wherein the at least one electrode is configured to measure an electrical signal based on a cardiac activation signal; receiving the electrical signal; providing an electrogram based on the electrical signal; determining at least one of a sharpness of the electrogram and a characteristic of a morphology of the electrogram, the characteristic of the morphology of the electrogram relating to the sharpness of the electrogram; and displaying an indication of at least one of the sharpness and the characteristic of the morphology, wherein the indication comprises at least one of a map, a light indicator, and a waveform.

In Example 56, the method of Example 55, wherein the catheter comprises an ablation catheter including a tissue ablation electrode configured to apply ablation energy to tissue, the method further comprising performing an ablation of a portion of the tissue.

In Example 57, the method of Example 56, further comprising determining the characteristic of the morphology of the electrogram before an ablation, during an ablation, and/or after an ablation.

In Example 58, the method of Example 55, further comprising filtering, using a filter, the electrical signal to generate a filtered signal.

In Example 59, the method of Example 58, wherein the electrical signal is unipolar, and wherein filtering the electrical signal comprises applying a nonlinear processing technique to the electrogram to retain only negative deflections.

In Example 60, the method of Example 59, wherein applying the nonlinear processing technique comprises applying a half-wave rectifier to the electrogram.

In Example 61, the method of Example 58, wherein filtering the electrical signal comprises approximating a derivative of the electrical signal, the method further comprising determining a relative change in an amplitude of the filtered signal during a period of time, wherein the indication of the characteristic of the morphology indicates the relative change in the amplitude of the filtered signal during the period of time.

In Example 62, the method of Example 61, wherein the amplitude comprises at least one of an absolute amplitude, a root-mean-squared (RMS) measurement, a peak-to-peak measurement, a maximum of a peak-to-peak measurement over a window, a percentile range measurement, a beat-gated measurement, and a free-running measurement.

In Example 63, the method of Example 58, wherein the filter is more responsive to high-frequency and/or quickly-varying components of the electrical signal than to low-frequency and/or slowly-varying components of the electrical signal.

In Example 64, the method of Example 55, further comprising: filtering the electrical signal across a first time scale, using a first filter, to generate a first filtered signal, wherein the first filter comprises a first frequency response; filtering the electrical signal across a second time scale, using a second filter, to generate a second filtered signal, wherein the second filter comprises a second frequency response, wherein at least a portion of the frequency response of the second filter is lower than a corresponding portion of the frequency response of the first filter; determining a feature corresponding to sharpness by analyzing the first and second filtered signals; and providing an output to a display device, wherein the output comprises the determined feature, wherein the display device is configured to depict a change in the determined feature over time.

In Example 65, the method of Example 64, wherein at least one of the first and second filters is configured to determine at least one of a time difference of the electrical signal, a derivative of the electrical signal, a slope estimate across a time window, and a wavelet decomposition of the electrical signal.

In Example 66, the method of Example 64, wherein at least one of the first and second filters is more responsive to high-frequency and/or quickly-varying components of the electrical signal than to low-frequency and/or slowly-varying components of the electrical signal.

In Example 67, the method of Example 64, further comprising determining an overall morphology change of the electrogram based on a pre-ablation deflection template.

In Example 68, the method of Example 67, wherein the change in morphology is determined using at least one of a matched filter, a correlation, and a convolution with the pre-ablation deflection template or a signal derived therefrom.

In Example 69, the method of Example 64, the waveform representing at least one of the filtered signal, an envelope of the filtered signal, an amplitude of the filtered signal, and a power of the filtered signal.

In Example 70, the method of Example 65, further comprising determining a combined signal comprising a combination of the filtered signal with an additional filtered signal, the waveform representing at least one of the combined signal, an envelope of the combined signal, an amplitude of the combined signal, and a power of the combined signal.

In Example 71, a system includes an ablation catheter including a flexible catheter body having a distal portion, a tissue ablation electrode disposed on the distal portion of the flexible catheter body, wherein the tissue ablation electrode is configured to apply ablation energy to tissue. The system also includes at least one electrode disposed on the distal portion, the at least one electrode configured to measure an electrical signal based on a cardiac activation signal; and a radiofrequency (RF) generator operatively coupled to the tissue ablation electrode and configured to generate the ablation energy to be conveyed to the tissue ablation electrode. The system further includes a mapping processor configured to: acquire the electrical signal from the at least one electrode; provide an electrogram based on the electrical signal; determine at least one of a sharpness associated with the electrogram and a characteristic of a morphology of the electrogram, the characteristic relating to the sharpness.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
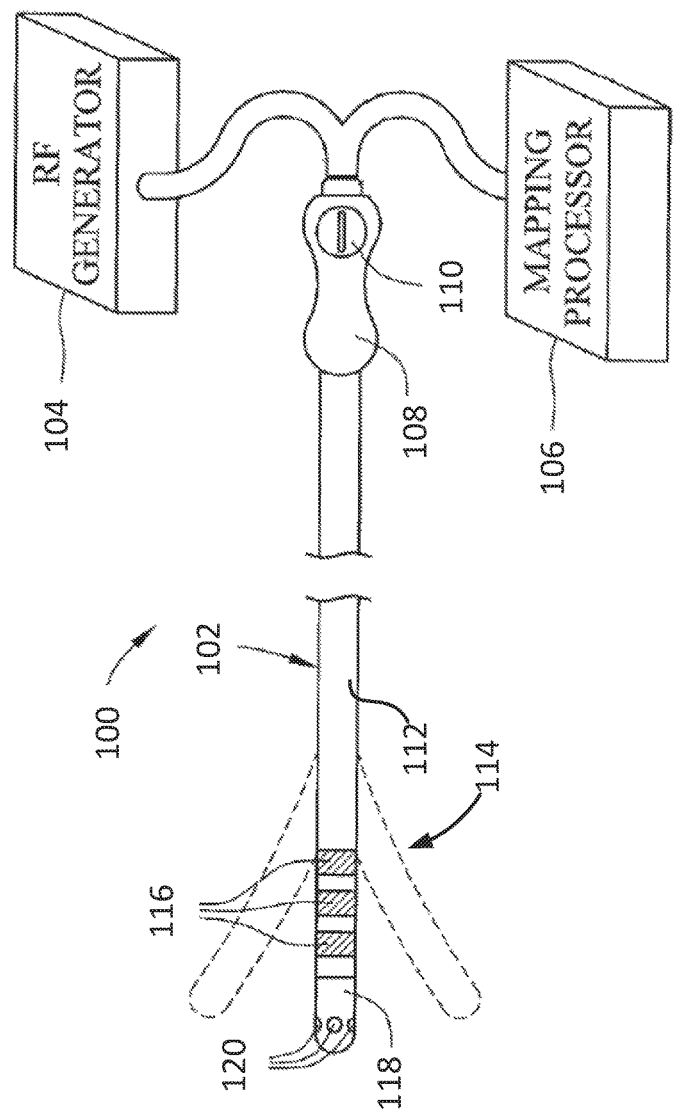
FIG. 1 is a schematic illustration of a radio frequency (RF) ablation system in accordance with embodiments of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Electrophysiologists may utilize any number of metrics to assess the formation and transmurality of lesions. These include, for example, bipolar electrogram amplitude drop, ablation impedance drop, and pacing capture threshold. Electrogram amplitude, measured from peak to peak of a given bipolar electrogram deflection, provides a measure of myocardium viability. However, it does not quantify the morphology of the electrogram, which may contain additional information about lesion formation, especially in unhealthy tissue. In unhealthy tissue (e.g., tissue afflicted by edema, scar tissue, etc.), amplitude reduction due to damage to the local surviving tissue may be obscured by the much stronger far-field signal. However, damage to the local tissue may make some components of the electrogram change less rapidly as compared to when the local tissue was healthy. Quantifying electrogram morphology before, during, and after an ablation, by analyzing sharpness of the electrogram, may facilitate aiding electrophysiologists in evaluating the formation of lesions. Real-time morphology analysis may facilitate enabling electrophysiologists to determine a minimum amount of time required for each ablation, reducing the amount of radiofrequency (RF) energy delivered during procedures.

According to various embodiments, measuring sharpness may include assigning a time-varying value to an electrogram. For example, sharpness may be quantified using an approximate derivative calculated at various temporal scales. The values may be used, in a relative manner, throughout an ablation in order to gauge the progressive change of morphology. Embodiments of the invention may be implemented using specialty catheters or catheters already commercially available. Embodiments include a hardware/software graphical user interface (GUI) used for acquiring electrical signals, performing sharpness analyses, and displaying the results during an ablation procedure. This may be accomplished, for example, with a stand-alone system or may be incorporated into existing systems such as the Bard LabSystem Pro or the Rhythmia Mapping System, both available from Boston Scientific Corporation of Marlborough, Mass.

FIG. 1 is a schematic illustration of a radio frequency (RF) ablation system 100 in accordance with embodiments of the present invention. As shown in FIG. 1, the system 100 includes an ablation catheter 102, an RF generator 104, and a mapping processor 106. The ablation catheter 102 is operatively coupled to both the RF generator 104 and the mapping processor 106, as will be described in greater detail herein. As is further shown, the ablation catheter 102 includes a proximal handle 108 having an actuator 110 (e.g., a control knob, lever, or other actuator), a flexible body 112 having a distal portion 114 including a plurality of ring electrodes 116, a tissue ablation electrode 118, and a plurality of mapping electrodes 120 (also referred to herein as "pin" electrodes) disposed or otherwise positioned within and/or electrically isolated from the tissue ablation electrode 118. In various embodiments, the catheter system 100 may also include noise artifact isolators (not shown), wherein the electrodes 120 are electrically insulated from the exterior wall by the noise artifact isolators.

In some instances, the ablation system 100 may be utilized in ablation procedures on a patient and/or in ablation procedures on other objects. In various embodiments, the ablation catheter 102 may be configured to be introduced into or through the vasculature of a patient and/or into or through any other lumen or cavity. In an example, the ablation catheter 102 may be inserted through the vasculature of the patient and into one or more chambers of the patient's heart (e.g., a target area). When in the patient's vasculature or heart, the ablation catheter 102 may be used to map and/or ablate myocardial tissue using the ring electrodes 116, the electrodes 120 and/or the tissue ablation electrode 118. In embodiments, the tissue ablation electrode 118 may be configured to apply ablation energy to myocardial tissue of the heart of a patient.

The catheter 102 may be steerable to facilitate navigating the vasculature of a patient or navigating other lumens. For example, the distal portion 114 of the catheter 102 may be configured to be deflected (as indicated by the dashed outlines in FIG. 1) by manipulation of the actuator 110 to effect steering the catheter 102. In some instances, the distal portion 114 of the catheter 102 may be deflected to position the tissue ablation electrode 118 and/or the electrodes 120 adjacent target tissue or to position the distal portion 114 of the catheter 102 for any other purpose. Additionally, or alternatively, the distal portion 114 of the catheter 102 may have a pre-formed shape adapted to facilitate positioning the tissue ablation electrode 118 and/or the electrodes 120 adjacent a target tissue. For example, the preformed shape of the distal portion 114 of the catheter 102 may include a radial shape (e.g., a generally circular shape or a generally semi-circular shape) and/or may be oriented in a plane transverse to a general longitudinal direction of the catheter 102.

In various embodiments, the electrodes 120 are circumferentially distributed about the tissue ablation electrode 118 and electrically isolated therefrom. The electrodes 120 can be configured to operate in unipolar or bipolar sensing modes. In some embodiments, the plurality of electrodes 120 may define and/or at least partially form one or more bipolar electrode pairs, each bipolar electrode pair being configured to measure an electrical signal corresponding to a sensed electrical activity (e.g., an electrogram (EGM) reading) of the myocardial tissue proximate thereto. The measured signals from the electrodes 120 can be provided to the mapping processor 106 for processing as described herein. In embodiments, an EGM reading or signal from a bipolar electrode pair may at least partially form the basis of a contact assessment, ablation area assessment (e.g., tissue viability assessment), and/or an ablation progress assessment (e.g., a lesion formation/maturation analysis), as discussed below.

Various embodiments may include, instead of, or in addition to, an ablation catheter 102, a mapping catheter (not shown) that includes mapping electrodes such as, for example, the electrodes 120, but does not necessarily include a tissue ablation electrode 118. In embodiments, for example, a mapping catheter may be utilized for mapping while performing an ablation with a separate ablation catheter (e.g., the ablation catheter 102), or independently of performing tissue ablation. In other embodiments, more than one mapping catheter may be used to enhance the mapping data. Additionally or alternatively to the circumferentially spaced electrodes 120, the catheter 102 may include one or more forward facing electrodes (not shown). The forward facing electrodes may be generally centrally located within the tissue ablation electrode 118 and/or at an end of a tip of the catheter 102.

The tissue ablation electrode 118 may be any length and may have any number of the electrodes 120 positioned therein and spaced circumferentially and/or longitudinally about the tissue ablation electrode 118. In some instances, the tissue ablation electrode 118 may have a length of between one (1) mm and twenty (20) mm, three (3) mm and seventeen (17) mm, or six (6) mm and fourteen (14) mm. In one illustrative example, the tissue ablation electrode 118 may have an axial length of about eight (8) mm.

In some cases, the plurality of electrodes 120 may be spaced at any interval about the circumference of the tissue ablation electrode 118. In one example, the tissue ablation electrode 118 may include at least three electrodes 120 equally or otherwise spaced about the circumference of the tissue ablation electrode 118 and at the same or different longitudinal positions along the longitudinal axis of the tissue ablation electrode 118. In some illustrative instances, the tissue ablation electrode 118 may have an exterior wall that at least partially defines an open interior region (not shown). The exterior wall may include one or more openings for accommodating one or more electrodes 120. Additionally, or alternatively, the tissue ablation electrode 118 may include one or more irrigation ports (not shown). Illustratively, the irrigation ports, when present, may be in fluid communication with an external irrigation fluid reservoir and pump (not shown) which may be used to supply fluid (e.g., irrigation fluid) to myocardial tissue to be or being mapped and/or ablated.

The RF generator 104 may be configured to deliver ablation energy to the ablation catheter 102 in a controlled manner in order to ablate the target tissue sites identified by the mapping processor 106. Ablation of tissue within the heart is well known in the art, and thus for purposes of brevity, the RF generator 104 will not be described in further detail. Further details regarding RF generators are provided in U.S. Pat. No. 5,383,874, which is expressly incorporated herein by reference in its entirety for all purposes. Although the mapping processor 106 and RF generator 104 are shown as discrete components, they can alternatively be incorporated into a single integrated device.

The RF ablation catheter 102 as described may be used to perform various diagnostic functions to assist the physician in an ablation treatment. For example, in some embodiments, the catheter 102 may be used to ablate cardiac arrhythmias, and at the same time provide real-time assessment of a lesion formed during RF ablation. Real-time assessment of the lesion may involve any of monitoring surface and/or tissue temperature at or around the lesion, reduction in the electrocardiogram signal, a drop in impedance, direct and/or surface visualization of the lesion site, and imaging of the tissue site (e.g., using computed tomography, magnetic resonance imaging, ultrasound, etc.). In addition, the presence of the electrodes within the RF tip electrode can operate to assist the physician in locating and positioning the tip electrode at the desired treatment site, and to determine the position and orientation of the tip electrode relative to the tissue to be ablated.

Illustrative catheters that may be used as the catheter 102 may include, among other ablation and/or mapping catheters, those described in U.S. patent application Ser. No. 12/056,210 filed on Mar. 26, 2008, and entitled HIGH RESOLUTION ELECTROPHYSIOLOGY CATHETER, and U.S. Pat. No. 8,414,579 filed on Jun. 23, 2010, entitled MAP AND ABLATE OPEN IRRIGATED HYBRID CATHETER, which are both hereby incorporated herein by reference in their entireties for all purposes. Alternatively, or in addition, catheters that may be used as the catheter 102 may include, among other ablation and/or mapping catheters, those described in U.S. Pat. No. 5,647,870 filed on Jan. 16, 1996, as a continuation of U.S. Ser. No. 206,414, filed Mar. 4, 1994 as a continuation-in-part of U.S. Ser. No. 33,640, filed Mar. 16, 1993, entitled MULTIPLE ELECTRODE SUPPORT STRUCTURES, U.S. Pat. No. 6,647,281 filed on Apr. 6, 2001, entitled EXPANDABLE DIAGNOSTIC OR THERAPEUTIC APPARATUS AND SYSTEM FOR INTRODUCING THE SAME INTO THE BODY, and U.S. Pat. No. 8,128,617 filed on May 27, 2008, entitled ELECTRICAL MAPPING AND CRYO ABLATING WITH A BALLOON CATHETER, which are all hereby incorporated herein by reference in their entireties for all purposes.

In operation and when the catheter 102 is within a patient and/or adjacent a target area, the catheter 102 may sense electrical signals (e.g., EGM signals) from the patient or target area and relay those electrical signals to a physician (e.g., through the display of the RF ablation system 100). Electrophysiologists and/or others may utilize an EGM amplitude and/or EGM morphology to verify a location of the ablation catheter in a patient's anatomy, to verify viability of tissue adjacent the ablation catheter, to verify lesion formation in tissue adjacent the ablation catheter, and/or to verify or identify other characteristics related to the catheter 102 and/or adjacent target tissue or areas.

Based, at least in part, on its sensing capabilities, the catheter 102 may be utilized to perform various diagnostic functions to assist the physician in ablation and/or mapping procedures, as referred to above and discussed further below. In one example, the catheter 102 may be used to ablate cardiac arrhythmias, and at the same time provide real-time positioning information, real-time tissue viability information, and real-time assessment of a lesion formed during ablation (e.g., during RF ablation). Real-time assessment of the lesion may involve monitoring surfaces and/or tissue temperature at or around the lesion, reduction in the electrogram signal amplitude and/or spectrum, a change in impedance (e.g., an increase or decrease), direct and/or surface visualization of the lesion site, and/or imaging of a tissue site (e.g., using computed tomography, magnetic resonance imaging, ultrasound, etc.). "Real-time", as used herein and understood in the art, means during an action or process. For example, where one is monitoring frequency spectra in real time during an ablation at a target area, the frequency spectra are being monitored during the process of ablating at a target area (e.g., between applications of ablation energy). Additionally, or alternatively, the presence of electrodes 120 at or about the tissue ablation electrode 118 and/or within the tip (e.g., at the distal tip) of the catheter 102 may facilitate allowing a physician to locate and/or position the tissue ablation electrode 118 at a desired treatment site, to determine the position and/or orientation of the tissue ablation electrode relative to the tissue that is to be ablated or relative to any other feature.

Figure 2:
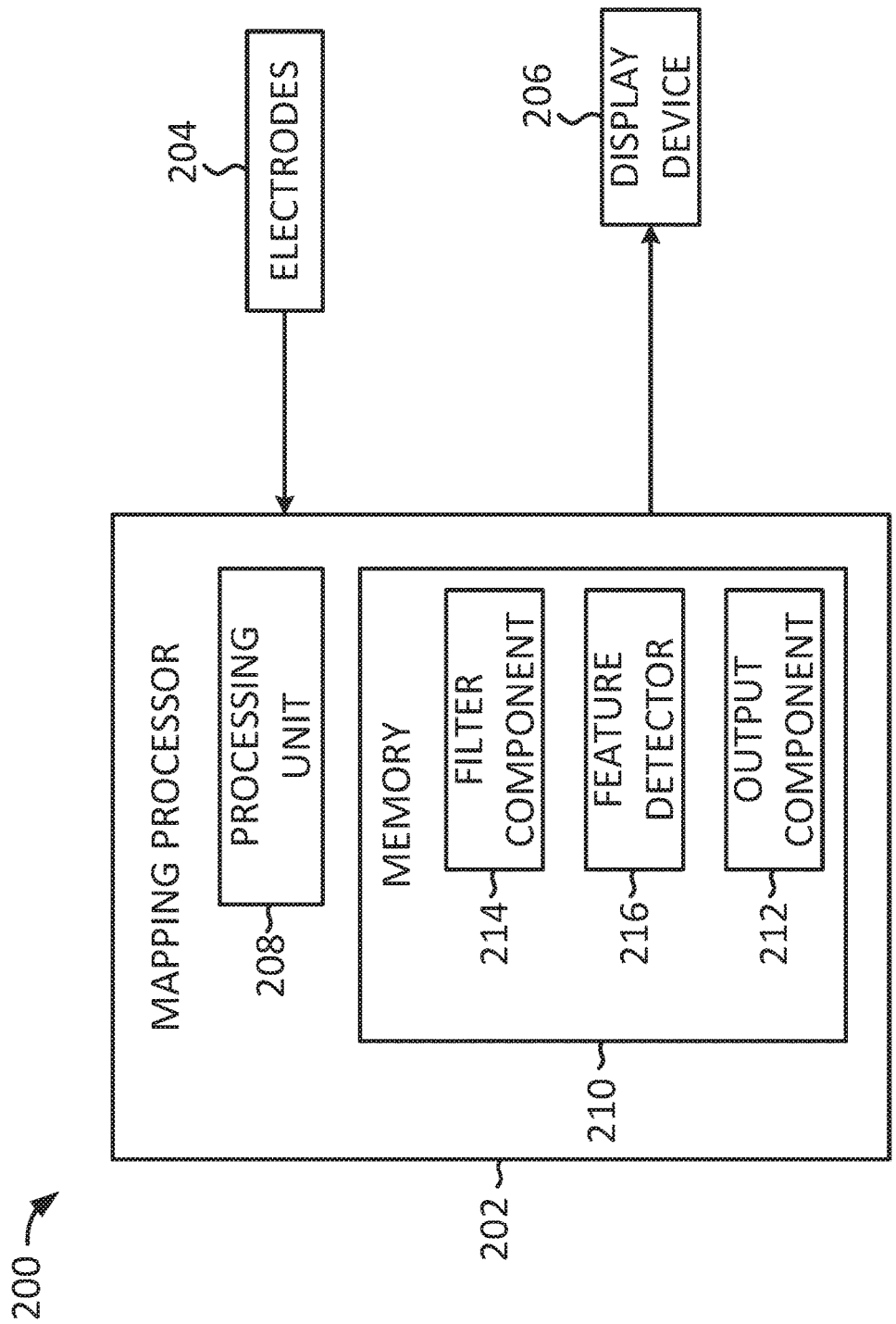
FIG. 2 is a block diagram depicting an illustrative mapping operating environment in accordance with embodiments of the present invention.

FIG. 2 depicts an illustrative mapping operating environment 200 in accordance with embodiments of the present invention. In various embodiments, a mapping processor 202 (which may be, or be similar to, mapping processor 106 depicted in FIG. 1) may be configured to detect, process, and record electrical signals associated with myocardial tissue via a catheter such as the ablation catheter 102 depicted in FIG. 1, a mapping catheter, and/or the like. In embodiments, based on these electrical signals, a physician can identify the specific target tissue sites within the heart, and ensure that the arrhythmia causing substrates have been electrically isolated by the ablative treatment. The mapping processor 202 is configured to process signals from electrodes 204 (which may include, e.g., electrodes 120 and/or ring electrodes 116 depicted in FIG. 1), and to generate an output to a display device 206. The display device 206 may be configured to present an indication of a tissue condition, effectiveness of an ablation procedure, and/or the like (e.g., for use by a physician). In some embodiments, the display device 206 may include electrocardiogram (ECG) information, which may be analyzed by a user to determine the existence and/or location of arrhythmia substrates within the heart and/or determine the location of an ablation catheter within the heart. In various embodiments, the output from the mapping processor 202 can be used to provide, via the display device 206, an indication to the clinician about a characteristic of the ablation catheter and/or the myocardial tissue being mapped.

In instances where an output is generated to a display device 206 and/or other instances, the mapping processor 202 may be operatively coupled to or otherwise in communication with the display device 206. In embodiments, the display device 206 may include various static and/or dynamic information related to the use of an RF ablation system (e.g., the RF ablation system 100 depicted in FIG. 1). For example, the display device 206 may present an image of the target area, an image of the catheter, and/or information related to EGMs, which may be analyzed by the user and/or by a processor of the RF ablation system to determine the existence and/or location of arrhythmia substrates within the heart, to determine the location of the catheter within the heart, and/or to make other determinations relating to use of the catheter and/or other catheters.

In embodiments, the display device 206 may be an indicator. The indicator may be capable of providing an indication related to a feature of the output signals received from one or more of the electrodes 204. For example, an indication to the clinician about a characteristic of the catheter and/or the myocardial tissue interacted with and/or being mapped may be provided on the display device 206. In some cases, the indicator may provide a visual and/or audible indication to provide information concerning the characteristic of the catheter and/or the myocardial tissue interacted with and/or being mapped. In embodiments, the visual indication may take one or more forms. In some instances, a visual color or light indication on a display 206 may be separate from or included on an imaged catheter on the display 206 if there is an imaged catheter. Such a color or light indicator may include a progression of lights or colors that may be associated with various levels of a characteristic proportional to the amplitude and/or spectrum of an EGM. Alternatively, or in addition, an indicator indicating a level of a characteristic proportional to an amplitude and/or spectrum of an EGM may be provided in any other manner on a display and/or with any audible or other sensory indication, as desired.

In some cases, a visual indication may be an indication on a display device 206 (e.g., a computer monitor, touchscreen device, and/or the like) with one or more lights or other visual indicators. In one example of an indicator, a color of at least a portion of an electrode of a catheter imaged on a screen of the display 206 may change from a first color (e.g., red or any other color) when there is poor contact between the catheter and tissue to a second color (e.g., green or any other color different than the first color) when there is good contact between the catheter and the tissue and/or when ablation may be initiated after establishing good contact. Additionally or alternatively in another example of an indicator, when the amplitude and/or frequency spectrum of the EGM stops changing and/or reaches a lesion maturation amplitude or frequency spectrum threshold, a depicted color of an electrode on the imaged catheter may change colors to indicate a level of lesion maturation. In a similar manner, an indicator may be utilized to indicate a viability of tissue to be ablated. In the examples above, the changing color/light or changing other indicator (e.g., a number, an image, a design, etc.) may be located at a position on the display other than on the imaged catheter, as desired. According to embodiments, indicators may provide any type of information to a user. For example, the indicators discussed herein may be pass or fail type indicators showing when a condition is present or is not present and/or may be progressive indicators showing the progression from a first level to a next level of a characteristic.

According to embodiments, various components (e.g., the mapping processor 202) of the operating environment 200, illustrated in FIG. 2, may be implemented on one or more computing devices. A computing device may include any type of computing device suitable for implementing embodiments of the disclosure. Examples of computing devices include specialized computing devices or general-purpose computing devices such "workstations," "servers," "laptops," "desktops," "tablet computers," "hand-held devices," and the like, all of which are contemplated within the scope of FIG. 2 with reference to various components of the operating environment 200.

In embodiments, a computing device includes a bus that, directly and/or indirectly, couples the following devices: a processing unit (e.g., the processing unit 208 depicted in FIG. 2), a memory (e.g., the memory 210 depicted in FIG. 2), an input/output (I/O) port, an I/O component (e.g., the output component 212 depicted in FIG. 2), and a power supply. Any number of additional components, different components, and/or combinations of components may also be included in the computing device. The bus represents what may be one or more busses (such as, for example, an address bus, data bus, or combination thereof). Similarly, in embodiments, the computing device may include a number of processing units (which may include, for example, hardware, firmware, and/or software computer processors), a number of memory components, a number of I/O ports, a number of I/O components, and/or a number of power supplies. Additionally any number of these components, or combinations thereof, may be distributed and/or duplicated across a number of computing devices.

In embodiments, the memory 210 includes computer-readable media in the form of volatile and/or nonvolatile memory and may be removable, nonremovable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; or any other medium that can be used to store information and can be accessed by a computing device such as, for example, quantum state memory, and the like.

In embodiments, the memory 210 stores computer-executable instructions for causing the processing unit 208 to implement aspects of embodiments of system components and/or to perform aspects of embodiments of methods and procedures discussed herein. Computer-executable instructions may include, for example, computer code, machine-useable instructions, and the like such as, for example, program components capable of being executed by one or more processors associated with a computing device. Examples of such program components include a filter component 214 and a feature detector 216. Program components may be programmed using any number of different programming environments, including various languages, development kits, frameworks, and/or the like. Some or all of the functionality contemplated herein may also be implemented in hardware and/or firmware.

The illustrative operating environment 200 shown in FIG. 2 is not intended to suggest any limitation as to the scope of use or functionality of embodiments of the present disclosure. Neither should it be interpreted as having any dependency or requirement related to any single component or combination of components illustrated therein. Additionally, any one or more of the components depicted in FIG. 2 may be, in embodiments, integrated with various ones of the other components depicted therein (and/or components not illustrated), all of which are considered to be within the ambit of the present disclosure. For example, the filter component 214 may be integrated with the feature detector 216. In embodiments, any number of components such as those depicted in FIG. 2 may be utilized to analyze EGM data, as described herein.

For example, in embodiments, EGM amplitude may be determined and/or measured in real-time by the mapping processor 202, e.g., from peak to peak of an EGM deflection or from the ST segment of the P-QRS-T curve of an EGM reading or signal in a time domain, and may quantify an intensity of an EGM signal and provide information relating to one or more target area characteristics. In embodiments, some target area characteristics include, but are not limited to, contact force between the catheter 102 and tissue, viability of tissue, and lesion maturation.

In some instances, EGM data may be further analyzed in a meaningful manner in real-time (e.g., during a typical electrophysiology procedure) by determining a sharpness feature associated with the EGM and determining, based on the sharpness feature, a characteristic of morphology of the EGM. In embodiments, determining the sharpness feature may include filtering an EGM signal with the mapping processor 202 and/or other processor and analyzing the resulting filtered signal or signals. Such an analysis of filtered signals derived from an EGM signal may enhance EGM data interpretation and may allow for real-time insights related to contact assessments, viable versus non-viable tissue, and/or lesion maturation during an ablation procedure, among other real-time insights.

Illustratively, any technique, as desired, may be utilized (e.g., by the filter component 214) to filter an EGM signal. For example, the filter component 214 may be configured to determine an approximate derivative of the EGM signal, apply frequency filters to the EGM signal across various time scales, apply a half-wave rectifier or other nonlinear processing to unipolar EGM signals, apply matched filters to the EGM signal, and/or the like. In embodiments, for example, the filter component 214 may be configured to filter the EGM to generate a filtered signal, and the feature detector 216 may be configured to determine a feature (e.g., an amplitude, an envelope, a power, etc.) of the filtered signal. The filter component 214 may, in embodiments, include any number of nonlinear processing elements configured to attenuate one or more components of a signal, e.g., based on the polarity of the deflection of the signal. For example, a matched filter may be used to quantify overall morphology of the EGM. For example, the filter component 214 may select a pre-ablation deflection template (or signal derived therefrom) and correlate it, and/or convolute it, with one or more deflections received during and/or after ablation. In this manner, for example, the feature detector 216 may be used to determine a maximum normalized correlation of the template with each subsequent deflection, which may represent, for example, an amplitude-independent change in morphology of the EGM over time.

The output component 212 may be configured to provide an output to the display device 206, where the output includes the determined feature (e.g., an amplitude computed over a window such as a window that is related to one or more beat events) of the filtered signal. For example, the display device 206 may be configured to indicate a relative change in the amplitude of the filtered signal during a period of time. According to embodiments, the amplitude may include a root-mean-squared (RMS) amplitude calculation, a power calculation, a peak-to-peak calculation, a percentile range calculation, a beat-gated amplitude, a free-running amplitude, and/or the like. In embodiments, the display device 206 may be configured to display a waveform. The waveform may, for example, represent the filtered signal, an envelope of the filtered signal, an amplitude of the filtered signal, a power of the filtered signal, a combined signal (e.g., a combination of the filtered signal with an additional filtered signal), an envelope of a combined signal, an amplitude of a combined signal, a power of a combined signal, and/or the like. A combined signal may, for example, be generated by averaging the filtered signal and an additional filtered signal, computing a root mean square (RMS) of the two signals, and/or the like.

Figure 3:
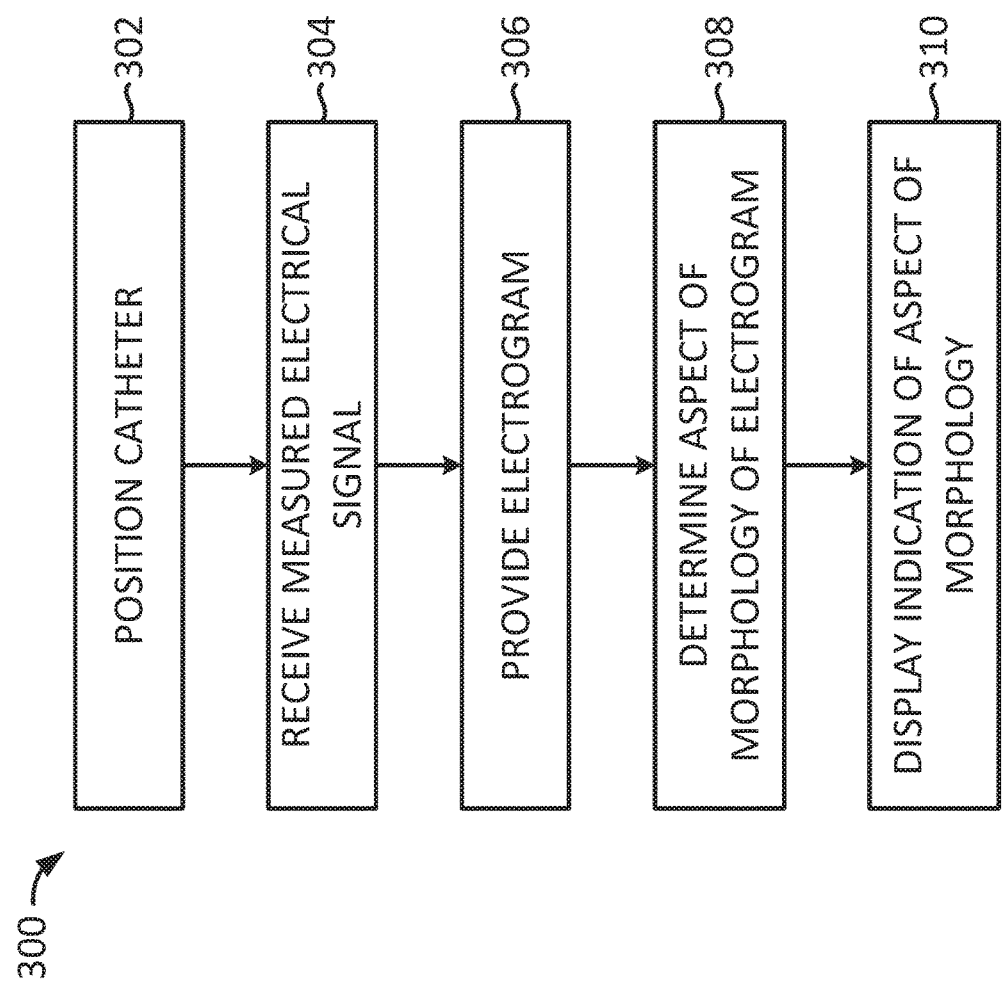
FIG. 3 is a flow diagram depicting an illustrative method of analyzing morphology of an electrogram in accordance with embodiments of the present invention.

As described above, in embodiments, a mapping processor (e.g., the mapping processor 106 depicted in FIG. 1 and/or the mapping processor 202 depicted in FIG. 2) may utilize sharpness features of an electrogram (EGM) to analyze morphology of the EGM. FIG. 3 depicts an illustrative method 300 of analyzing morphology of an electrogram in accordance with embodiments of the present invention. In the illustrative method 300, a distal portion of a catheter (e.g., the catheter 102 depicted in FIG. 1, a mapping catheter, and/or the like) may be positioned at a location proximate a target area or target tissue (block 302). A mapping processor (e.g., the mapping processor 106 depicted in FIG. 1 and/or the mapping processor 202 depicted in FIG. 2) may receive electrical signal measurements from one or more electrodes (e.g., the ablation electrode 118 depicted in FIG. 1, the electrodes 120 depicted in FIG. 1, the electrodes 204 depicted in FIG. 2, and/or other electrodes) of the catheter (e.g., the catheter 102 depicted in FIG. 1) adjacent a target area or tissue (block 304). Illustratively, the signals measured by the electrodes of the catheter may be used to provide an EGM (block 306). Providing the EGM may include sampling, resampling, quantizing, band-pass filtering, noise removal, and/or other processing steps to prepare the signal for use in the mapping processor. As is further shown in FIG. 3, embodiments of the illustrative method 300 further include determining a characteristic of morphology of the EGM (block 308) and displaying an indication of the characteristic of morphology (block 310).

According to embodiments, the mapping processor determines a characteristic of morphology of the EGM based on a sharpness feature of the EGM. In embodiments, the mapping processor may filter the EGM (e.g., the electrical signal) to generate a filtered signal and determine a relative change in an amplitude of the filtered signal during a period of time. For example, the mapping processor may filter the EGM by determining an approximate derivative of the measured electrical signal, in which case the indication of the characteristic of the morphology may indicate the relative change in the amplitude of the filtered signal during the period of time, a representation of an envelope of the filtered signal, and/or the like. In embodiments, the mapping processor may determine an approximate first derivative of the EGM, an approximate second derivative of the EGM, and/or approximate derivatives of higher order. In embodiments, by discretely differentiating an EGM over a sliding time window, the mapping processor may emphasize high frequencies and evaluate the relative change in the amplitude of that differentiated EGM at activation times. Approximating a derivative may include applying a filter with a frequency response that increases roughly in proportion to frequency over some frequency range, e.g. a first difference or a first-order high-pass filter. Approximating a derivative may also include estimating the slope of a signal over some time scale, e.g. using a filter that outputs the slope of a linear regression over a sliding time window.

In some instances, an amplitude, relative amplitude, change in amplitude, and/or rate of change in amplitude of the measured electrical signal (e.g., the EGM), filtered signal, and/or the like, may also be identified and/or represented in an indication via a display device (e.g., the display device 206 depicted in FIG. 2). In an illustrative example, the amplitude of a measured electrical signal may be the amplitude of the ST-segment of a P-QRS-T wave of an EGM. Additionally or alternatively, other amplitudes of an electrical signal may be identified. According to embodiments, amplitudes, relative amplitudes, envelopes, and/or the like of an electrical signal (or a filtered signal) may be compared to, combined with, or otherwise analyzed in conjunction with similar measures associated with one or more filtered signals. For instance, providing an indication of the characteristic of morphology may include displaying a waveform that is generated by combining (e.g., via an averaging technique, determining a root mean square (RMS), etc.) one or more filtered signals and/or an electrical signal (e.g., the EGM).

According to embodiments, a level of one or more characteristics may be represented and/or monitored via the determined characteristics of morphology of the EGM. The one or more characteristics may include, for example, contact force between the catheter and a target area (e.g., a target tissue or other target area), viability of a target area, ablation progress (e.g., lesion maturation or other metric of ablation progress), and conduction characteristics of a target area. In embodiments, one or more of these or other characteristics can be represented and/or monitored, as described herein, in real time, for example, while positioning the distal portion of the catheter proximate the target area, while mapping a target area or other object, while applying ablation energy to a target area, and/or while performing any other action with the catheter. The level of the one or more of the characteristics may be displayed visually on a display, may be indicated by an audible indicator, or may be indicated in any other manner. In embodiments, the indication may include a map (e.g., a voltage map, a frequency spectral map, etc.), a light indicator, a waveform, and/or the like.

For example, the EGM signals and/or filtered signals may be displayed on a display or screen for viewing and/or analysis by a user (e.g., a physician, technician, or other user) of the ablation system and/or mapping catheter. As an alternative, or in addition, to displaying the EGM signals and/or filtered signals, an indication of the orientation of the ablation catheter with respect to a target cardiac tissue may be displayed on a display with indicators thereon or thereabout indicating characteristics proportional to the EGM signals and/or filtered signals. Such an indication of the orientation of the catheter may facilitate the user of the ablation system in determining the orientation of the catheter with respect to the target cardiac tissue. A user of the ablation system may manipulate the catheter to modify a position of the catheter with respect to a target cardiac tissue or to change a force applied to the target cardiac tissue in order to obtain various EGM signal readings. Such manipulation of the catheter may facilitate determining the viability of the target/sensed cardiac tissue, as explained, for example, in U.S. Provisional Application No. 61/955,087, "ELECTROPHYSIOLOGY SYSTEM," filed Mar. 18, 2014; and U.S. application Ser. No. 13/738,562, "ELECTROPHYSIOLOGY SYSTEM AND METHODS," filed Jan. 10, 2013, each of which is hereby incorporated herein by reference in its entirety for all purposes.

Figure 4:
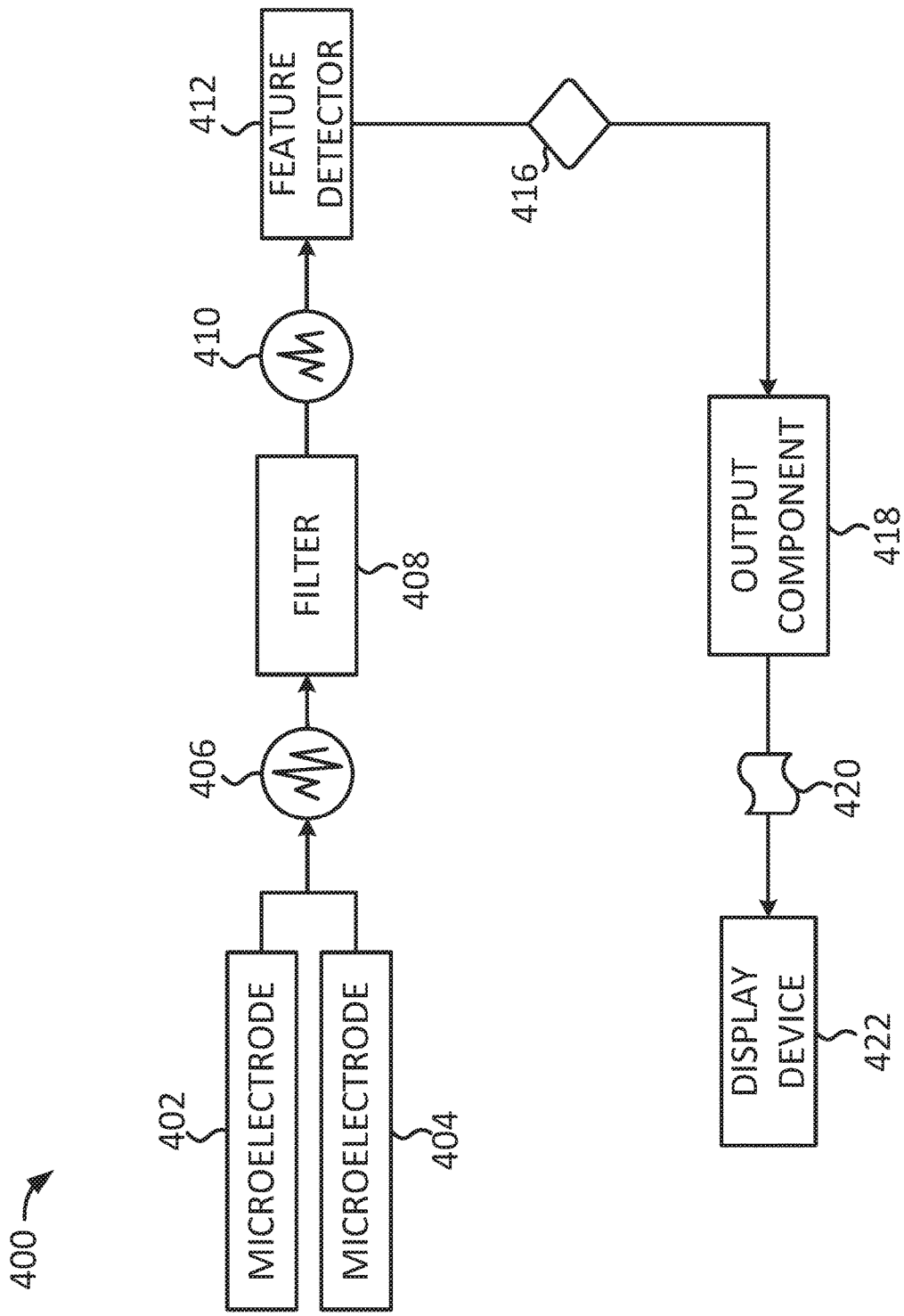
FIG. 4 is a schematic block diagram depicting an illustrative process flow for analyzing morphology of an electrogram in accordance with embodiments of the present invention.
Figure 5:
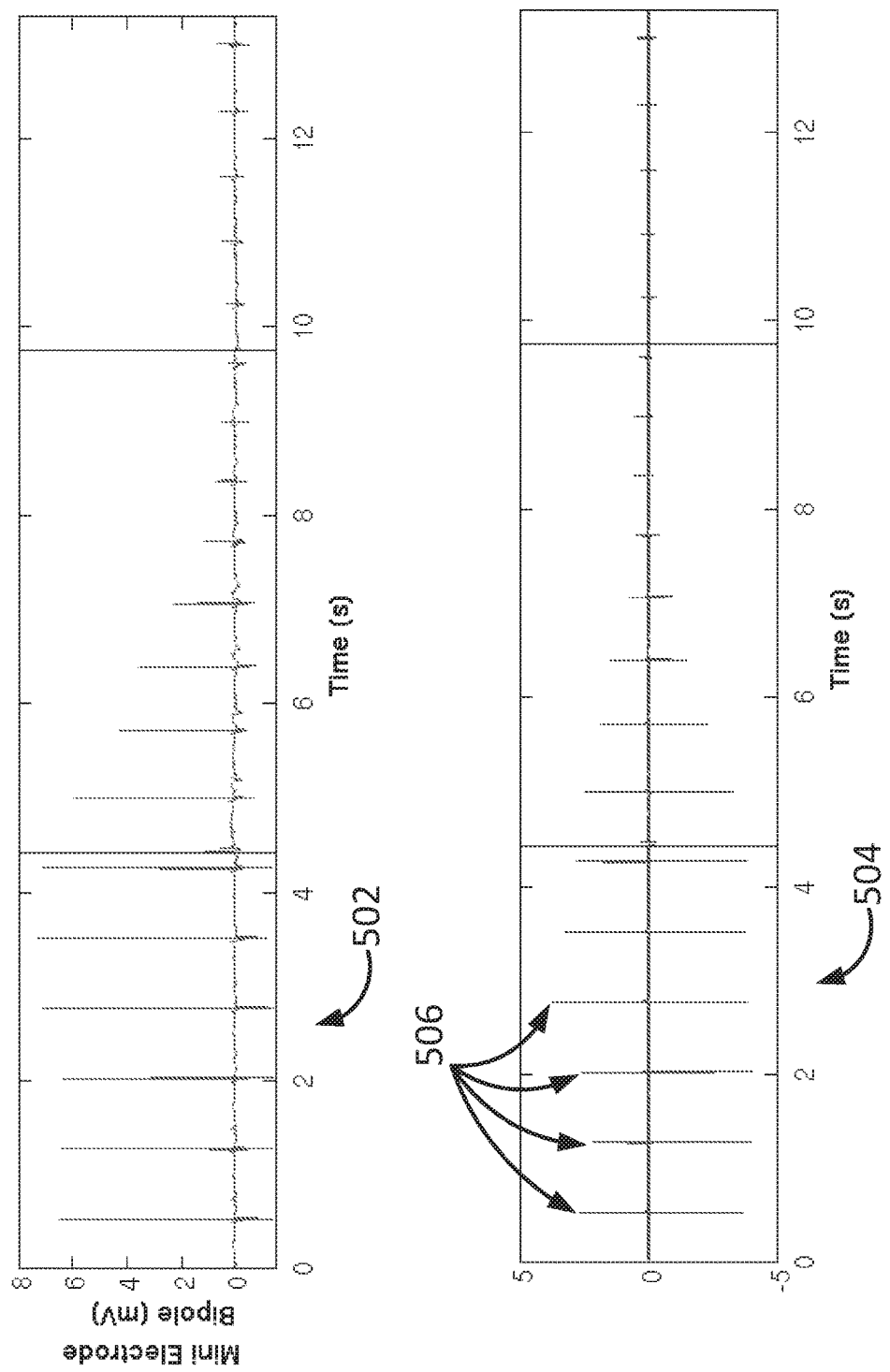
FIG. 5 depicts an illustrative electrogram and filtered electrogram in accordance with embodiments of the present invention.

FIG. 4 depicts an illustrative process flow 400 for analyzing morphology of an electrogram in accordance with embodiments of the present invention. As shown in FIG. 4, a pair of electrodes 402, 404 provide a measured electrical signal 406 (e.g., an electrogram) to a filter 408. As discussed above, the electrodes 402, 404 may be, for example, the electrodes 120 depicted in FIG. 1, and may be configured to measure the electrical signal 406 in response to electrical activity detected in myocardial tissue. The filter 408 is configured to filter the measured electrical signal 406 to generate a filtered signal 410. In embodiments, for example, the filter 408 may be, include, or be included within the filter component 214 depicted in FIG. 2. In embodiments, the filtered signal 408 may include one or more derivatives of the electrical signal 406. FIG. 5 depicts an example of an electrical signal 502 measured by electrodes, in this case, a bipolar electrogram. In embodiments, the filter 408 may be configured to determine a first derivative 504 of the electrical signal 502. Although the first derivative 504 is depicted in FIG. 5, in implementations of embodiments of the present invention, the filtered signal 504 need not necessarily be displayed, but may be maintained in a memory as a set of data.

Returning to FIG. 4, the filtered signal 410 is provided to a feature detector 412, which determines a feature 416 of the filtered signal 410. In embodiments, for example, the feature 416 of the filtered signal 410 may include one or more amplitudes (e.g., peak amplitudes 506 depicted in FIG. 5) of the filtered signal 410, an envelope of the filtered signal 410, a frequency or aspect of frequency spectrum of the filtered signal 410, and/or the like. The feature 416 of the filtered signal is received by an output component 418 (e.g., the output component 212 depicted in FIG. 2). In embodiments, the output component 418 is configured to provide an output 420 to a display device 422. The output may include, for example, the determined feature 416 of the filtered signal 410 such as, for example, a set of determined amplitudes of a derivative of the measured electrical signal 406, a measure of a relative change in the amplitude of the filtered signal 410 during a period of time, a waveform corresponding to the envelope of the filtered signal 410, a curve fitted to the amplitudes of the peaks of the filtered signal 410, a numerical representation of one or more of the foregoing, an executable instruction, and/or any other signal configured to cause the display device 422 to display an indication of a characteristic of the morphology of the measured electrical signal 406. As discussed above, the indication may include, for example, a map, a light indicator, and/or a waveform.

The illustrative process flow 400 shown in FIG. 4 is not intended to suggest any limitation as to the scope of use or functionality of embodiments of the present invention. Neither should the illustrative process flow 400 be interpreted as having any dependency or requirement related to any single component or combination of components illustrated therein. That is, for example, the process flow 400 may include any number of filters 408. Additionally, any one or more of the components depicted in FIG. 4 may be, in embodiments, integrated with various ones of the other components depicted therein (and/or components not illustrated), all of which are considered to be within the ambit of the present invention.

Figure 6:
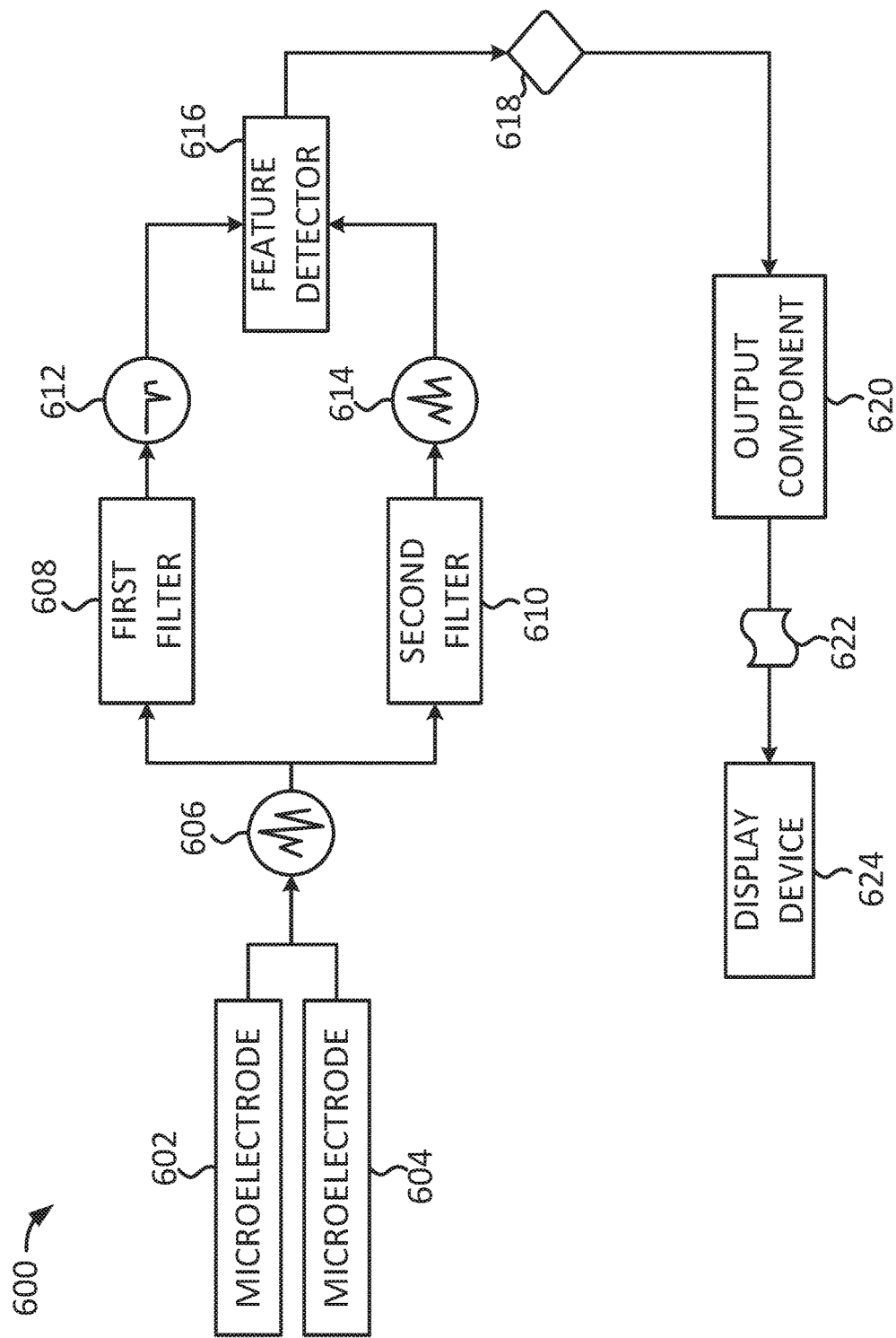
FIG. 6 is a schematic block diagram depicting another illustrative process flow for analyzing morphology of an electrogram in accordance with embodiments of the present invention.

FIG. 6 depicts another illustrative process 600 for analyzing morphology of an electrogram in accordance with embodiments of the present invention. As shown in FIG. 6, a pair of electrodes 602, 604 provide a measured electrical signal 606 (e.g., an electrogram) to a first filter 608 and a second filter 610. As discussed above, the electrodes 602, 604 may be, for example, the electrodes 120 depicted in FIG. 1, and may be configured to measure the electrical signal 606 in response to electrical activity detected in myocardial tissue. As shown in FIG. 6, the first filter 608 filters the measured electrical signal 606 to generate a first filtered signal 612, and the second filter 610 filters the measured electrical signal 606 to generate a second filtered signal 614. The first and second filtered signals 612 and 614 are provided to a feature detector 616 that is configured to determine a feature corresponding to sharpness of the electrical signal 606 by analyzing the first and second filtered signals 612 and 614. The determined feature 618 is provided to an output component 620 that is configured to provide an output 622 to a display device 624, which may, for example, be configured to depict a change in the determined feature 618 over time.

According to embodiments, the first filter 608 may include a first filter, having a first frequency response, configured to filter the electrical signal 606 across a first time scale to generate the first filtered signal 612. The first filtered signal 612 may, for example, include a first frequency spectrum. Additionally, the second filter 610 may include a second filter, having a second frequency response, configured to filter the electrical signal 606 across a second time scale to generate a second filtered signal 614, and where the second filtered signal 614 includes a second frequency spectrum. In embodiments, at least a portion of the spectrum of the second filtered signal may be lower than a corresponding portion of the frequency spectrum of the first filtered signal. Additionally, in embodiments, the first filter and/or the second filter may be more responsive to high-frequency, and/or quickly-varying components, of the measured electrical signal than to low-frequency, and/or slowly-varying components of the measured electrical signal. High-frequency, low-frequency, quickly-varying, and slowly-varying components of the signal may be determined based on any number of different thresholds or ranges. In embodiments, the filter or filters may be configured to be more responsive to various components such that detection of characteristics of the sharpness of the measured electrical signal, as described herein, is enhanced and/or optimized.

According to various embodiments, at least one of the first and second filters 608 and 610 is configured to determine at least one of a time difference of the measured electrical signal 606, a derivative of the measured electrical signal 606, a slope estimate across a time window, and a wavelet decomposition of the measured electrical signal 606. In embodiments, the feature detector 616 may be configured to combine information corresponding to the first and second filtered signals 612 and 614 across time scales to assess sharpness. For example, the feature detector 616 may be configured to compare filtered signal levels at different scales (e.g., short-term vs. long-term slope) to determine an amplitude-invariant measure of sharpness. In embodiments, the feature detector 616 may be configured to evaluate any number of different characteristics associated with a comparison between the first and second filtered signals such as, for example, frequency or phase shifts, frequency spectrum tilt (e.g., an increase in the amount of high or low frequencies over time as amplitudes decrease), and/or the like.

The illustrative process flow 600 shown in FIG. 6 is not intended to suggest any limitation as to the scope of use or functionality of embodiments of the present invention. Neither should the illustrative process flow 600 be interpreted as having any dependency or requirement related to any single component or combination of components illustrated therein. That is, for example, the process flow 600 may include any number of filters 608, 610. Moreover, the filters 608 and 610 may be configured to operate in series. That is, for example, the second filter 610 may be configured to filter the first filtered signal 612 rather than the electrical signal 606. Additionally, any one or more of the components depicted in FIG. 6 may be, in embodiments, integrated with various ones of the other components depicted therein (and/or components not illustrated), all of which are considered to be within the ambit of the present invention.

Various modifications and additions can be made to the exemplary embodiments discussed without departing from the scope of the present invention. For example, while the embodiments described above refer to particular features, the scope of this invention also includes embodiments having different combinations of features, embodiments having additional features, and embodiments that do not include all of the described features. Accordingly, the scope of the present invention is intended to embrace all such alternatives, modifications, and variations as fall within the scope of the claims, together with all equivalents thereof.

For example, while bipolar signals have an advantage of reducing far-field signals, one disadvantage is that information in the polarity of deflection may be lost. In a bipolar electrogram, local tissue depolarization may appear as a positive deflection, a negative deflection, or both. In a unipolar electrogram (which can be processed to reduce far-field signals), only negative deflections are indicative of local tissue depolarization. Therefore, embodiments of the present invention, as described herein, may be configured to include a nonlinear processing step to retain only negative deflections, e.g., by a half-wave rectifier after filtering the unipolar EGM, which may result in reduced noise floor and better spatial selectivity.

We claim:

1. A system comprising:
   a catheter including:
      a flexible catheter body having a distal portion; and
      at least one electrode disposed on the distal portion, the at least one electrode configured to measure an electrical signal based on a cardiac activation signal; and
   a mapping processor configured to:
      acquire the electrical signal from the at least one electrode;
      provide an electrogram based on the electrical signal;
      determine a sharpness feature associated with the electrogram and, based on the determined sharpness feature, determine a characteristic of a morphology of the electrogram, wherein the characteristic of the morphology of the electrogram is related to the sharpness.

2. The system of claim 1, wherein the catheter comprises an ablation catheter including a tissue ablation electrode configured to apply ablation energy to tissue, the system further comprising a radiofrequency (RF) generator operatively coupled to the tissue ablation electrode, wherein the RF generator is configured to generate the ablation energy and convey the generated ablation energy to the tissue ablation electrode, and wherein the mapping processor is configured to determine the sharpness before an ablation, during an ablation, and/or after an ablation.

3. The system of claim 1, further comprising a display device, wherein the mapping processor comprises:

a filter configured to filter the electrical signal to generate a filtered signal;

a feature detector configured to determine an amplitude of the filtered signal; and an output component configured to provide an output to the display device, wherein the output comprises the determined amplitude of the filtered signal.

4. The system of claim 3, wherein the amplitude comprises at least one of an absolute amplitude, a root-mean-squared (RMS) measurement, a peak-to-peak measurement, a maximum of a peak-to-peak measurement over a window, a percentile range measurement, a beat-gated measurement, and a free-running measurement.

5. The system of claim 3, wherein the filter is more responsive to high-frequency and/or quickly-varying components of the electrical signal than to low-frequency and/or slowly-varying components of the electrical signal.

6. The system of claim 3, wherein the filtered signal comprises an approximate derivative of the electrical signal.

7. The system of claim 3, wherein the filter includes a nonlinear processing element configured to attenuate one or more components of the electrical signal based on a polarity of a deflection of the electrical signal.

8. The system of claim 7, wherein the filter comprises a half-wave rectifier.

9. The system of claim 3, wherein the display device is configured to indicate a relative change in the amplitude of the filtered signal during a period of time.

10. The system of claim 3, wherein the display device is configured to display a waveform representing at least one of the filtered signal, an envelope of the filtered signal, an amplitude of the filtered signal, and a power of the filtered signal.

11. The system of claim 10, wherein the output component is configured to determine a combined signal comprising a combination of the filtered signal with an additional filtered signal, the waveform representing at least one of the combined signal, an envelope of the combined signal, an amplitude of the combined signal, and a power of the combined signal.

12. The system of claim 1, further comprising a display device, the mapping processor comprising:

a first filter configured to filter the electrical signal across a first time scale to generate a first filtered signal, wherein the first filter comprises a first frequency response;

a second filter configured to filter the electrical signal across a second time scale to generate a second filtered signal, wherein the second filter comprises a second frequency response, wherein at least a portion of the frequency response of the second filter is lower than a corresponding portion of the frequency response of the first filter;

a feature detector configured to determine a feature corresponding to sharpness by analyzing the first and second filtered signals; and an output component configured to provide an output to the display device, wherein the output comprises the determined feature, wherein the display device is configured to depict a change in the determined feature over time.

13. The system of claim 12, wherein at least one of the first and second filters is configured to determine at least one of a time difference of the electrical signal, an approximate derivative of the electrical signal, a slope estimate across a time window, and a wavelet decomposition of the electrical signal.

14. The system of claim 12, wherein at least one of the first and second filters is more responsive to high-frequency and/or quickly-varying components of the electrical signal than to low-frequency and/or slowly-varying components of the electrical signal.

15. The system of claim 12, wherein the feature detector is configured to assess the sharpness of the electrical signal by comparing one or more levels of the first filtered signal with one or more levels of the second filtered signal to determine an amplitude-invariant measure of sharpness.

16. The system of claim 1, wherein the mapping processor is further configured to determine an overall morphology change of the electrogram based on a pre-ablation deflection template.

17. The system of claim 16, wherein the change in morphology is determined using at least one of a matched filter, a correlation, and a convolution with the pre-ablation deflection template or a signal derived therefrom.

18. A method for evaluating a condition of myocardial tissue, the method comprising:

positioning a catheter adjacent to myocardial tissue within a patient's body, the catheter comprising:
a flexible catheter body having a distal portion; and
at least one electrode disposed on the distal portion, the at least one electrode configured to measure an electrical signal based on a cardiac activation signal;

receiving the electrical signal;

providing an electrogram based on the electrical signal;

determining a sharpness feature of the electrogram;

determining, based on the determined sharpness feature of the electrogram, a characteristic of a morphology of the electrogram, the characteristic of the morphology of the electrogram relating to the sharpness of the electrogram; and displaying an indication of at least one of the sharpness and the characteristic of the morphology, wherein the indication comprises at least one of a map, a light indicator, and a waveform.

19. The method of claim 18, further comprising:

filtering the electrical signal across a first time scale, using a first filter, to generate a first filtered signal, wherein the first filter comprises a first frequency response;

filtering the electrical signal across a second time scale, using a second filter, to generate a second filtered signal, wherein the second filter comprises a second frequency response, wherein at least a portion of the frequency response of the second filter is lower than a corresponding portion of the frequency response of the first filter;

determining a feature corresponding to sharpness by analyzing the first and second filtered signals; and providing an output to a display device, wherein the output comprises the determined feature, wherein the display device is configured to depict a change in the determined feature over time.

20. A system comprising:

an ablation catheter including:
a flexible catheter body having a distal portion;
a tissue ablation electrode disposed on the distal portion of the flexible catheter body, wherein the tissue ablation electrode is configured to apply ablation energy to tissue;
at least one electrode disposed on the distal portion, the at least one electrode configured to measure an electrical signal based on a cardiac activation signal; and a radiofrequency (RF) generator operatively coupled to the tissue ablation electrode and configured to generate the ablation energy to be conveyed to the tissue ablation electrode; and a mapping processor configured to:
  acquire the electrical signal from the at least one electrode;
  provide an electrogram based on the electrical signal;
  determine a sharpness feature associated with the electrogram and, based on the determined sharpness feature, determine a characteristic of a morphology of the electrogram, the characteristic relating to the sharpness.

* * * * *